United States Patent [19]

Jones

[11] Patent Number: 5,843,458
[45] Date of Patent: Dec. 1, 1998

[54] RECOMBINANT HUMAN CYTOMEGALOVIRUS HAVING A US2 DELETION

[75] Inventor: Thomas R. Jones, New City, N.Y.

[73] Assignee: American Cyanamid Company, Madison, N.J.

[21] Appl. No.: 509,214

[22] Filed: Jul. 31, 1995

Related U.S. Application Data

[63] Continuation-in-part of Ser. No. 282,696, Jul. 29, 1994.

[51] Int. Cl.$^6$ .......................... A61K 39/245; C12N 7/01; C12N 7/04; C12N 15/63
[52] U.S. Cl. ..................................... 424/230.1; 435/172.1; 435/172.3; 435/235.1; 435/236; 435/320.1
[58] Field of Search ...................... 424/230.1; 435/172.1, 435/235.1, 236, 375, 320.1, 172.3

[56] References Cited

U.S. PATENT DOCUMENTS

| | | | |
|---|---|---|---|
| 4,058,598 | 11/1977 | Stern et al. | 424/230.1 |
| 4,877,612 | 10/1989 | Berger et al. | 424/282.1 |
| 4,877,737 | 10/1989 | Shih et al. | 424/205.1 |

FOREIGN PATENT DOCUMENTS

| | | |
|---|---|---|
| 0521427 | 1/1993 | European Pat. Off. . |
| WO89/10966 | 11/1989 | WIPO . |

OTHER PUBLICATIONS

Mikkelsen, T.R., et al.; Transgenic Research, vol. 1, No. 4, 164–169 (1992).

Kollert, Jons A. et al., J. Virology, vol. 65, No. 10, 1991, pp. 5184–5189.

Jones, T.R. et al., J. Virology, vol. 66, No. 4, 1992, pp. 2541–2546.

Chee M.S. et al., Current Topics in Microbiology and Immunology, vol. 154, 1990, pp. 126–169.

Gilbert, M.J. et al., J. Virology, vol. 67, No. 6, 1993, pp. 3461–3469.

Beersma, M.F.C. et al., J. Immunology, vol. 151, No. 9, 1993, pp. 4455–4464.

Jones, T.R. et al., J. Virology, vol. 69, No. 8, 1995, pp. 4830–4841.

Colberg–Poley, A. M. et al., J. Virology, vol. 66, No. 1, 1992, pp. 95–105.

Jones et al, J. of Virology, Nov., 1991, vol. 65 (11); pp. 5860–5872.

*Primary Examiner*—Terry A. McKelvey
*Attorney, Agent, or Firm*—Elizabeth M. Barnhard

[57] ABSTRACT

Infection of human fibroblast cells with human cytomegalovirus (HCMV) causes down-regulation of cell surface expression of MHC class I. A recombinant mutant HCMV which fails to down-regulate class I heavy chain expression is described. A method of controlling down-regulation of MHC class I expression in a cytomegalovirus infected cell, a pharmaceutical composition, a vaccine composition, a method of preventing or reducing susceptibility to acute cytomegalovirus in an individual, and a virus based gene therapy vector are also described.

6 Claims, 24 Drawing Sheets

RV7186 (IRS1–US11 DELETED)

RV798 (US2–US11 DELETED)

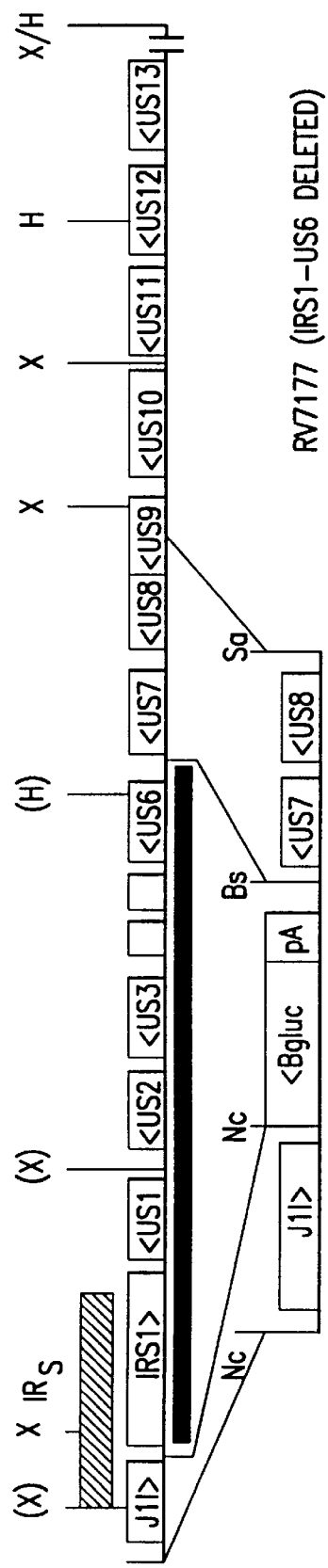
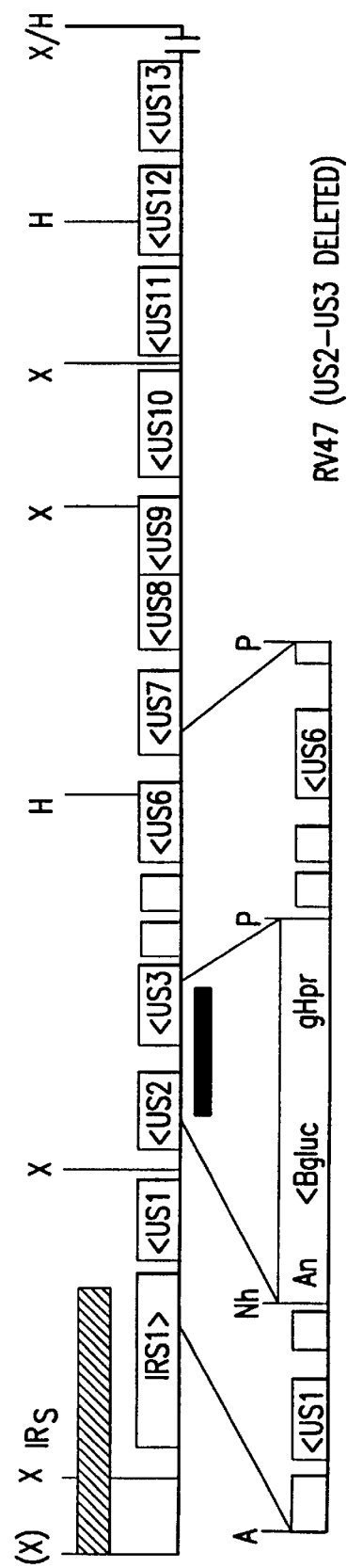
FIG. 1F
FIG. 1G

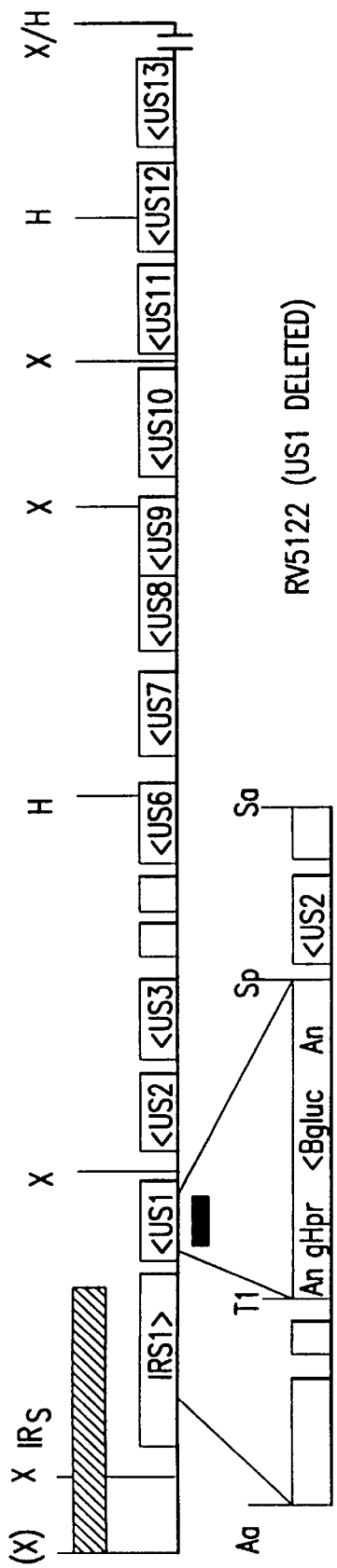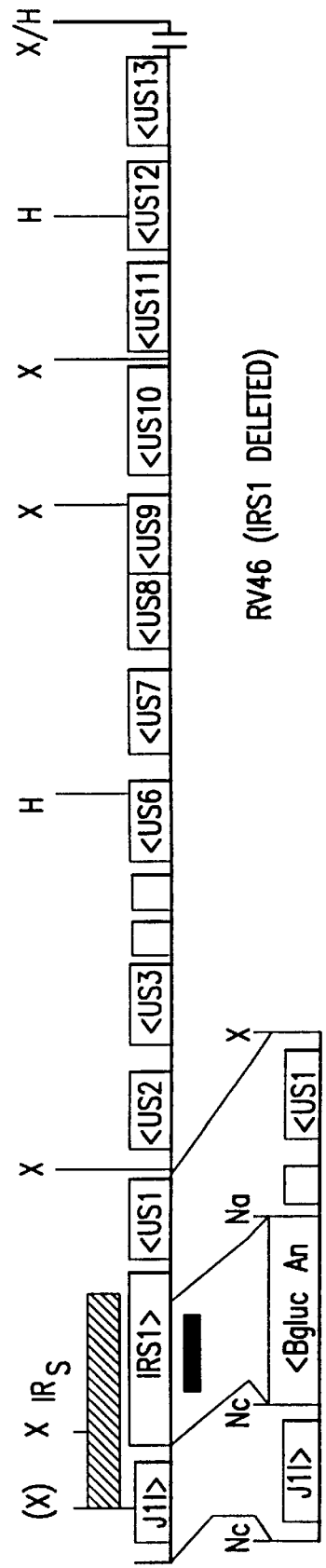
FIG. 1H
FIG. 1I

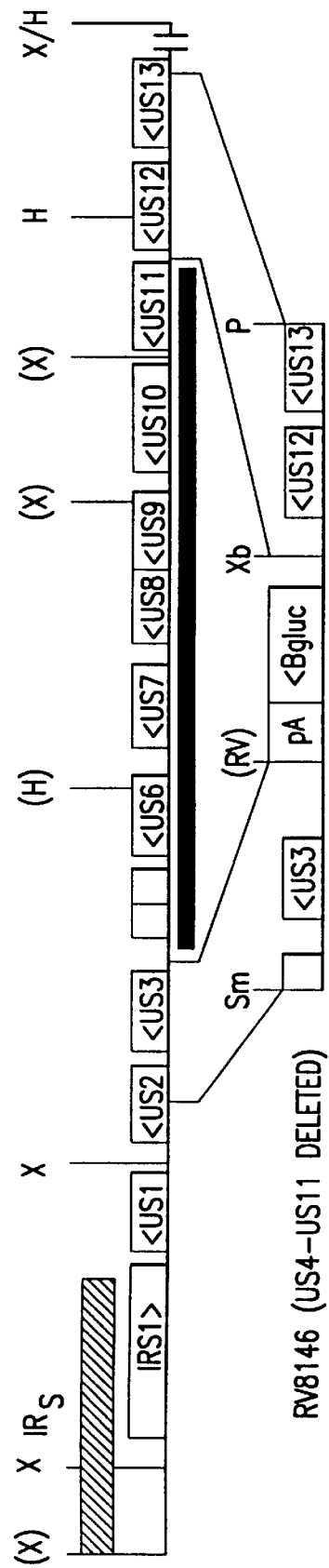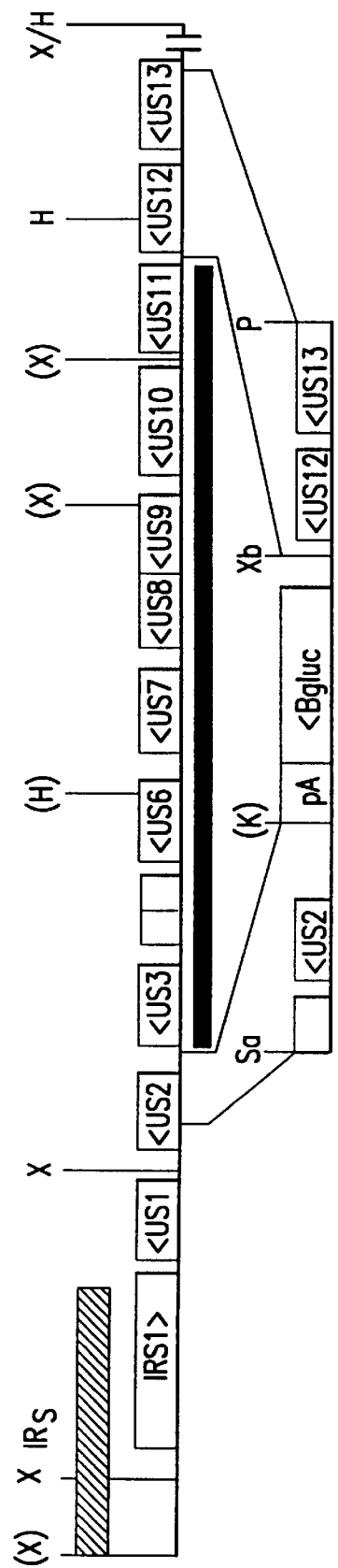

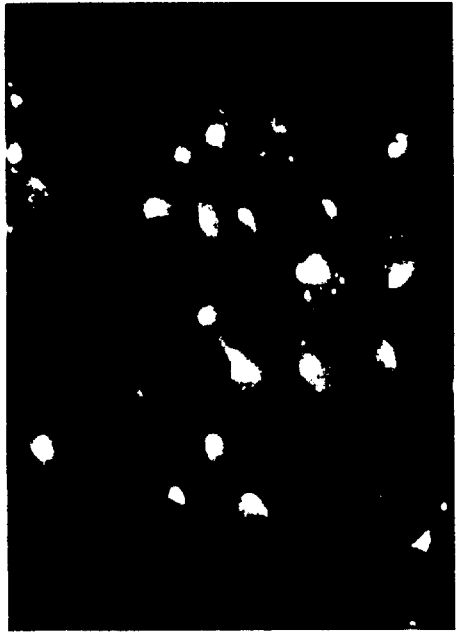
FIG.10B NONPERMEABILIZED AD169 (WT) 8h p.i.
FIG.10D RV699 8h p.i.
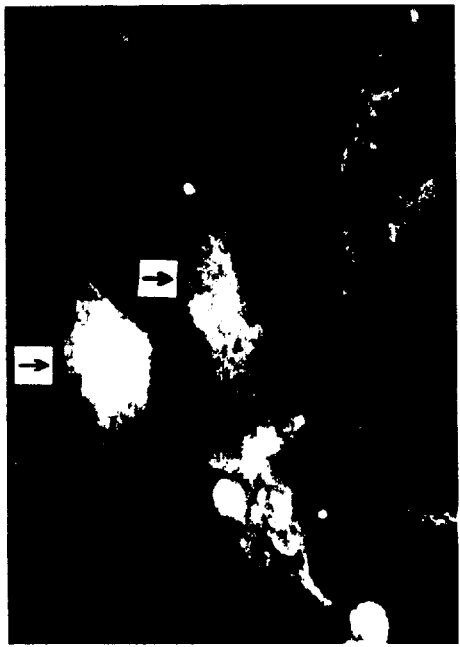
FIG.10A PERMEABILIZED AD169 (WT) 8h p.i.
FIG.10C RV699 8h p.i.

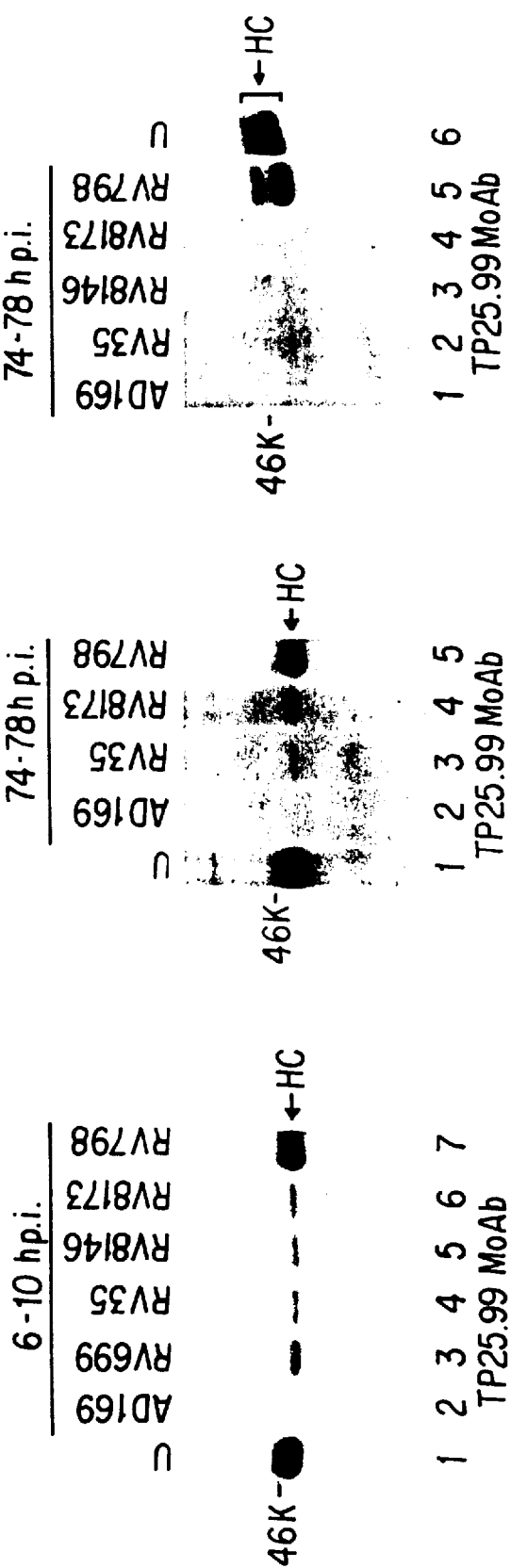

RECOMBINANT HUMAN CYTOMEGALOVIRUS HAVING A US2 DELETION

This is a continuation-in-part of copending application Ser. No. 08/282,696 filed on Jul. 29, 1994.

FIELD OF THE INVENTION

The present invention relates to recombinant mutant human cytomegalovirus (HCMV) which does not down-regulate expression of cellular MHC class I heavy chains upon infection and the identification of two human cytonegalovirus gene products sufficient to cause such down-regulation.

BACKGROUND OF THE INVENTION

Human cytomegalovirus (HCMV) is a betaherpesvirus which causes clinically serious disease in immunocompromised and immunosuppressed adults, as well as in some infants infected in utero or perinatally (Alford and Britt, 1990). In human cytomegalovirus (HCMV)-infected cells, expression of the cellular major histocompatibility complex (MHC) class I heavy chains is down-regulated. The 230-kb dsDNA genome of HCMV was sequenced (Chee et al., 1990) and has at least 200 open reading frames (ORFs). The functions of most of these 200 genes is unknown. For purposes of this application, open reading frame is defined as the portion of a gene which encodes a string of amino acids and hence may encode a protein. The function of some HCMV proteins are known or predicted due to their homology with other viral (esp. herpes simplex virus) and cellular proteins. However, for the majority of the HCMV ORFs, the function(s) of the proteins they encode is unknown.

In order to study HCMV gene function, HCMV deletion mutants can be constructed in order to assess their in vitro growth properties (Jones et al., 1991; Jones and Muzithras, 1992). For purposes of this application, deletion mutants are defined as human cytomegalovirus mutants which lack regions of the wild-type viral genome. This strategy involves site-directed replacement mutagenesis of selected HCMV gene(s) by a prokaryotic reporter gene, usually, β-glucuronidase, although guanosine phosphoribosyltransferase can also be used. In this fashion, the recombinant virus can be isolated only if the replaced viral gene(s) is nonessential.

Several investigators have shown that infection by HCMV results in the down-regulation of cellular MHC class I heavy chains (Browne et al., 1990; Beersma et al., 1993; Yamashita et al., 1993). For purposes of this application, down-regulation is defined as reduction in either synthesis, stability or surface expression of MHC class I heavy chains. Such a phenomenon has been reported for some other DNA viruses, including adenovirus, murine cytomegalovirus, and herpes simplex virus (Anderson et al., 1985; Burget and Kvist, 1985; del Val et al., 1989; Campbell et al., 1992; Campbell and Slater, 1994; York et al., 1994). In the adenovirus and herpes simplex virus systems, the product of a viral gene which is dispensable for replication in vitro is sufficient to cause down-regulation of MHC class I heavy chains (Anderson et al., 1985; Burget and Kvist, 1985). The gene(s) involved in class I heavy chain down-regulation by murine cytomegalovirus have not yet been identified.

SUMMARY OF THE INVENTION

The present invention provides a recombinant mutant human cytomegalovirus which does not down-regulate expression of cellular MHC class I heavy chains upon infection. A region of the genome of the recombinant cytomegalovirus (HCMV) mutant containing open reading frame US2 has been deleted.

The present invention also provides a method of controlling down-regulation of major histocompatibility complex (MHC) class I expression in a cytomegalovirus infected cell which utilizes the recombinant mutant human cytomegalovirus.

The present invention also provides a vaccine which utilizes the recombinant mutant human cytomegalovirus, as well as a method of immunizing an individual against cytomegalovirus employing the recombinant mutant human cytomegalovirus. A live attenuated HCMV vaccine lacking this gene region of open reading frame US2 will elicit a better immune response than one containing this gene region, based on the lack of class I down-regulation by the former. Therefore a virus lacking this region is a superior immunogen.

The present invention also provides a method of preventing or reducing susceptibility to acute cytomegalovirus in an individual by administering an immunogenic amount of the recombinant mutant human cytomegalovirus.

The present invention also provides a gene therapy vector in which the open reading frame US2 of the HCMV gene involved in the MHC class I heavy chain down-regulation can be incorporated into adenovirus vectors or similar virus based gene therapy vectors to minimize the immune response. This will allow the use of the recombinant adenovirus or similar virus based gene therapy vectors to be used in gene therapy.

The invention may be more fully understood by reference to the following drawings.

BRIEF DESCRIPTION OF THE DRAWINGS

FIGS. 1A–1J show organization of recombinant virus genomes. FIG. 1A, the first line, is a schematic of the overall organization of the HCMV wild-type genome. Unique region sequences are shown by a line, while repeated region sequences are indicated by shaded boxes. Relevant HindlII fragments, within the L and S components, are indicated by letter designation (Oram et al., 1982). The second line is an expansion of the wild-type HindlII-Q, -X, and -V regions of the S component. The significant open reading frames, and their orientation, are shown as open boxes (Chee et al., 1990). The position of the $IR_s$ repeated sequences is indicated by the shaded rectangle. The locations of HindlII (H) and Xhol (X) restriction endonuclease sites are shown. FIGS. 1B–I show the genomic organization of the indicated HCMV mutant. In each case, the first line is the organization of the parental AD169 wild-type genome, the second line represents the organization of relevant sequences of the linearized plasmid used to make the recombinant virus. The slanted lines indicate the boundaries of the viral flanking sequences which may be involved in homologous recombination to create the desired mutation. The region deleted is indicated by a shaded box below the first line. FIG. 1J shows the derivation and organization of RV799. The first two lines are the same representations as FIGS. 1B–I, with the third line representing the organization of the relevant sequences of the linearized plasmid used to make RV799 from the RV134 parent (second line). Restriction sites are: Apal (A), Aatll (Aa), Bsml (Bs), Hindill (H), Hpal (Hp), Narl (Na), Ncol (Nc), Nhel (Nh), Pstl (P), Sa/l (S), Saul (Sa), Sphl (Sp), Sstl (T1), Sstll (T2), Xbal (Xb), and Xhol (X).

FIGS. 2A–2C show organization of recombinant virus genomes. FIG. 2A, the first line, is a schematic of the overall organization of the HCMV wild-type genome. Unique region sequences are shown by a line, while repeated region sequences are indicated by shaded boxes. Relevant HindIII fragments, within the L and S components, are indicated by letter designation (Oram et al., 1982). The second line is an expansion of the wild-type HindIII-Q, -X, and -V regions of the S component. The significant open reading frames, and their orientation, are shown as open boxes (Chee et al., 1990). The position of the $IR_s$ repeated sequences is indicated by the shaded rectangle. The locations of Hindlil (H) and XhoI (X) restriction endonuclease sites are shown. FIGS. 2B and 2C show the genomic organization of the indicated HCMV mutant. In each case, the first line is the organization of the parental AD169 wild-type genome, the second line represents the organization of relevant sequences of the linearized plasmid used to make the recombinant virus. The slanted lines indicate the boundaries of the viral flanking sequences which may be involved in homologous recombination to create the desired mutation. The region deleted is indicated by a shaded box below the first line. Restriction sites are: EcoRV (RV), HindIII (H), KpnI (K), PstI (P), SacI (Sa), SmaI (Sm), XbaI (Xb), and XhoI (X). Sites in parentheses no longer exist in the recombinant virus.

FIG. 4A is a Western blot analysis. HFF cells were uninfected (U) or infected at a multiplicity of infection of 5 PFU/cell. At 24, 48, and 72 h post-infection, total cellular proteins were harvested, electrophoresed through a 15% SDS-polyacrylamide gel, electroblotted to nitrocellulose, and probed with TP25.99 murine monoclonal antibody (specific for a non-conformational epitope on MHC class I heavy chains) using an ECL chemiluminescent detection kit (Amersham). FIGS. 4B and 4C are immunoprecipitation analyses. HFF cells were uninfected or infected (as above), either in the absence or presence (+PFA) of phosphonoformate and radiolabeled either for 4 h at late times post-infection (69–73 h) (FIG. 4B) or for 2 h at the indicated time post-infection (FIG. 4C). Proteins were harvested immediately after radiolabeling and class I heavy chains were immunoprecipitated using TP25.99 murine monoclonal antibody.

FIG. 5A is a radiograph of class I heavy chains which were immunoprecipitated using TP25.99 murine monoclonal antibody. FIG. 5B is a radiograph of total radiolabeled proteins to verify approximately equivalent radiolabeling efficiency.

FIG. 6A is a radiograph of class I heavy chains which were immunoprecipitated using TP25.99 murine monoclonal antibody. Equivalent radiolabeling efficiency (FIG. 6B) and progression through the viral replicative cycle (FIG. 6C) were verified as described for FIG. 5B and C.

FIG. 8A is a radiograph of class I heavy chains which were immunoprecipitated using TP25.99 murine monoclonal antibody. Equivalent radiolabeling efficiency (FIG. 8B) and progression through the viral replicative cycle (FIG. 8C) were verified as described for FIG. 5B–C.

In FIG. 9A, the first line is the overall organization of the HCMV wild-type genome, and the second line is an expansion of the wild-type HindIII-Q and -X regions of the S component. The ORFs are indicated by an unshaded rectangle; the unlabeled ORF overlapping US4 and US5 is US4.5. In FIG. 9B, the deletions within the various HCMV mutants are indicated by the shaded rectangle. RV670 is deleted of IRS1-US9 and US11; RV35 is deleted of US6-US11; RV67 is deleted of US10-US11; RV80 is deleted of US8-US9; RV725 is deleted of US7; RV69 is deleted of US6; RV47 is deleted of US2-US3; RV5122 is deleted of US1; RV46 is deleted of IRS1; RV798 is deleted of US2-US11; RV7181 is deleted of IRS1–US9; RV7177 is deleted of IRS1-US6; and RV7186 is deleted of IRS1-US11. MHC class I heavy chain down-regulation results are from immunoprecipitation experiments (using the heavy chain conformation-independent monoclonal antibody, TP25.99) in which HCMV-infected HFF cells were radiolabeled at late times post-infection. FIG. 9C shows the location of the two subregions which contain gene(s) which are sufficient for MHC class I heavy chain down-regulation. Subregion A contains ORFs US2-US5 (bases 193119–195607) and subregion B contains ORFs US10 and US11 (bases 199083–200360).

FIGS. 10A–10D are photographs which show localization of US11 gene product (gpUS11) in infected cells by immunofluorescence. HFF cells were uninfected or infected with either AD169 wild-type or RV699 (deleted of the US11 gene) at a multiplicity of infection of 5 PFU/cell. After 8 h, uninfected and infected cells were fixed with 4% paraformaldehyde. Some cells were then permeabilized with 0.2% Triton X-100. The primary antibody was rabbit polyclonal antisera raised against a US11 fusion protein (Jones and Muzithras, 1991). Fluorescence was visualized through a Zeiss microscope.

FIGS. 11A–11C show immunoprecipitation of MHC class I heavy chains from cells infected with HCMV wild-type and mutants. HFF or U373-MG cells were uninfected (U) or infected with the indicated virus (multiplicity of infection of 5 or 3 PFU/cell, respectively) and radiolabeled for 4 h at the indicated time post-infection. Infected cell proteins were extracted immediately after radiolabeling and subject to immunoprecipitation by the anti-human MHC class I heavy chain monoclonal antibody TP25.99. HFF cells were radiolabeled at either early times (FIG. 11A) or late times (FIG. 11B) post-infection. U373-MG cells were radiolabeled at late times post-infection (FIG. 11C). AD169 is the HCMV wild-type strain from which the deletion mutant viruses were derived. RV699 is deleted of the US11 gene only; RV35 is deleted of US6 through US11 genes; RV8146 is deleted of US4 through US11; RV8173 is deleted of US3 through US11; and RV798 is deleted of US2 through US11.

In FIG. 12A, the first line is the overall organization of the HCMV wild-type genome, and the second line is an expansion of the wild-type HindIII-Q and -X regions of the S component. The ORFs are indicated by an unshaded rectangle; the unlabeled ORF overlapping US4 and US5 is US4.5. The location of the loci which contain gene(s) which are sufficient for MHC class I heavy chain down-regulation are shown by black rectangles. One locus contains ORFs US2-US5 (bases 193119–195607) and the other locus is US11 (bases 199716–200360). In FIG. 12B, the deletions within the various HCMV mutants are indicated by the shaded rectangle. AD169 is the wild-type strain and has no deletions; RV798 is deleted of US2-US11; RV699 is deleted of US11 only; and RV35 is deleted of US6-US11. In FIG. 12C, RV8146 is deleted of US4-US11 and RV8173 is deleted of US3-US11. MHC class I heavy chain down-regulation results are from immunoprecipitation experiments using the anti-human MHC class I heavy chain conformation-independent monoclonal antibody, TP25.99 and metabolically radiolabeled proteins from HCMV wild-type- or mutant-infected cells.

FIG. 14A is a radiograph of class I heavy chains which were immunoprecipitated using TP25.99 murine monoclonal antibody. FIG. 14B is a radiograph in which, to verify approximately equal infection, the 72-kDa IE1 immediate-early protein was immunoprecipitated using the murine monoclonal antibody 9221. FIG. 14C is a radiograph of the immunoprecipitation of the cellular transferrin receptor with murine monoclonal antibody Ber-T9 to verify approximately equal expression of this glycoprotein. FIG. 14D is a radiograph of total radiolabeled proteins to verify approximately equivalent radiolabeling efficiency.

In FIG. 17A, HFF cells were infected with RV35 (deleted of US11 through US6; US2 is retained) at a multiplicity of infection of 5. At 3 days p.i., the cells were pulse-labeled for 0.5 h and infected cell proteins were either harvested immediately (P), or harvested after a chase period, either 0.5, 1, 2, or 3 h, in unlabeled media. Heavy chains (HC) were immunoprecipitated using the TP25.99 monoclonal antibody. The half-life of class I heavy chains in RV35-infected cells is about 0.5 h. Conversely, parallel experiments using uninfected or RV798-infected cells (not shown) indicated the heavy chains have a half-life of greater than 3 h. In FIG. 17B, similar pulse-chase radiolabeling-immunoprecipitation experiments were performed on U373-MG parental cells or stably-transfected cell lines 55-212 and 55-310. Unlike the 55-310 cell line which expresses readily detectable amounts of pUS2, neither U373-MG cells or the 55-212 cell line expresses US2. Class I heavy chains are stable in cells which do not express US2, but has a short half-life in pUS2-expressing cells (i.e. 55-310). In FIG. 17C, the same pulse-chase extracts used in FIG. 17B were used for a control immunoprecipitation by the Ber-T9 monoclonal antibody, which is specific for another cellular glycoprotein, the transferrin receptor (TfR). In all three cell lines, the stability and processing of the transferrin receptor is similar.

DESCRIPTION OF THE PREFERRED EMBODIMENTS

A recombinant HCMV mutant called RV670 has been constructed which expresses a marker gene (β-glucuronidase) in place of a group of viral genes (Jones and Muzithras, 1992). Upon infection of human fibroblast cells with this mutant, expression of the major histocompatibility complex (MHC) class I heavy chains is not reduced as it is when wild-type HCMV infects these cells.

Figure 9:
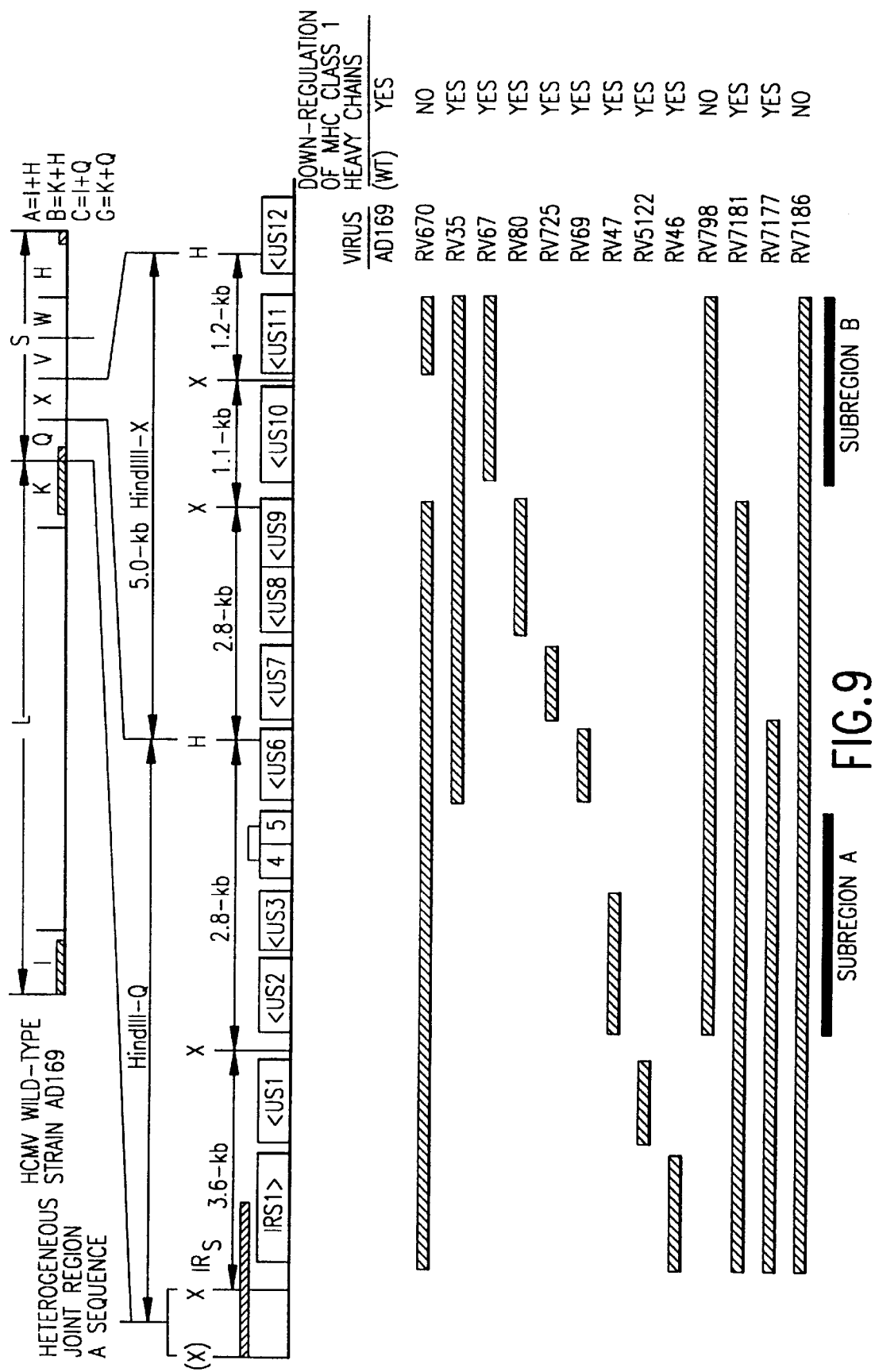
FIG. 9 provides a summary of MHC class I heavy chain expression data from HFF cells infected with wild-type and mutant HCMV.
Figure 12:
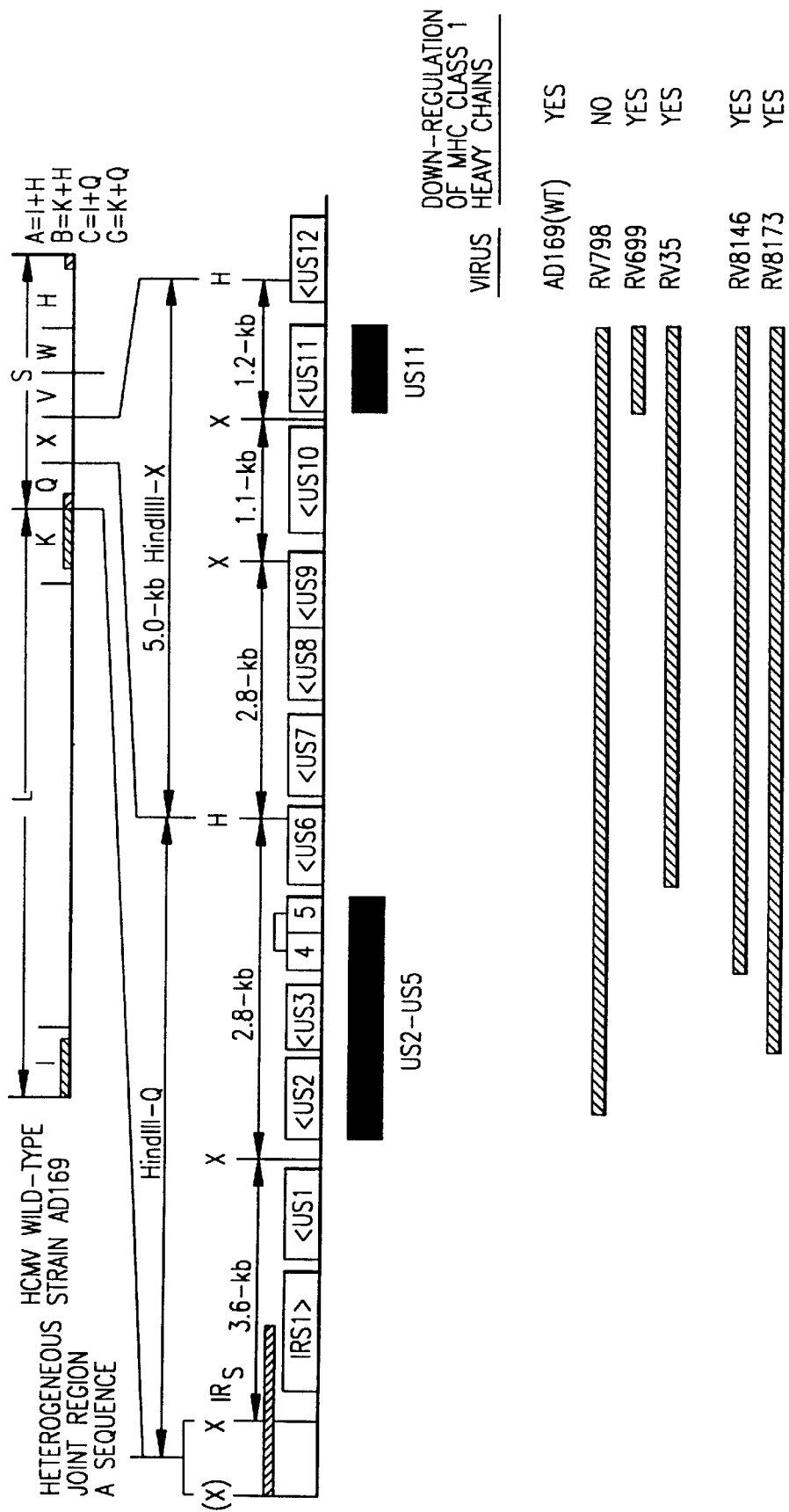
FIG. 12 provides a summary of MHC class I heavy chain expression data from HFF cells infected with wild-type and mutant HCMV.

Unlike wild-type HCMV, the present invention's recombinant HCMV mutant does not result in the down-regulation of cellular MHC class I heavy chain protein expression. Surprisingly, it has been found that a 7-kb region of the HCMV genome contains genes which are required for down-regulation of heavy chain expression and utilized in the invention. As described more fully below, are two genetic loci of HCMV in this 7-kb region which are independently sufficient for MHC class I heavy chain down-regulation. The US11 gene is one such locus, and the other locus is the US2-US5 gene subregion (i.e., subregion A). Both of these loci are within the 7-kb region of the HCMV genome from US2-US11, inclusive, which is deleted from the recombinant virus, RV798 (FIGS. 9 and 12). Correspondingly, RV798-infected cells do not down regulate MHC class I heavy chains. By the construction and analysis of other defined HCMV mutants, one locus has been found to be defined by the US11 gene, which was confirmed by other studies. US11 was expressed constitutively, at varying levels, in several stably-transfected cell lines. Analysis of protein expression in these cell lines indicated that expression of US11 was inversely correlated with that of MHC class I heavy chains. It has subsequently been found that the HCMV gene sufficient for MHC class I down-regulation within the second locus (US2-US5) is US2.

One skilled in the art will appreciate that efficient antigen processing and presentation is required to activate and expand cytotoxic T-lymphocyte precursors for an efficient cell mediated immune response. Efficient viral antigen presentation requires the continued expression of MHC class I proteins throughout infection. Infection of cells with RV670 results in continued expression of stable class I heavy chains.

One skilled in the art will appreciate that the virus (RV670) or another human cytomegalovirus with a deletion of similar genes (e.g. RV798), can be utilized to produce an effective live vaccine because class I heavy chains are still expressed in RV670-infected cells, as they are in uninfected cells, and therefore viral antigen presentation for the purpose of initiating a cytotoxic T cell response occurs.

Figure 4A:
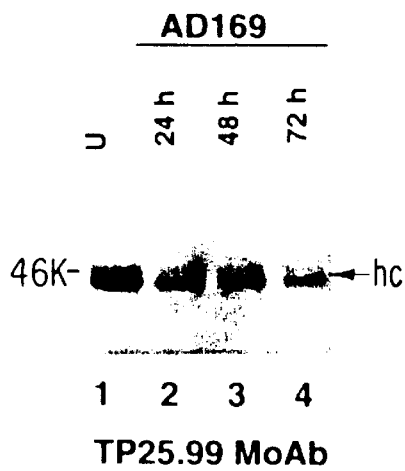
FIGS. 4A–4C show expression of MHC class I heavy chains in HCMV wild-type strain AD169-infected cells.
Figure 4C:
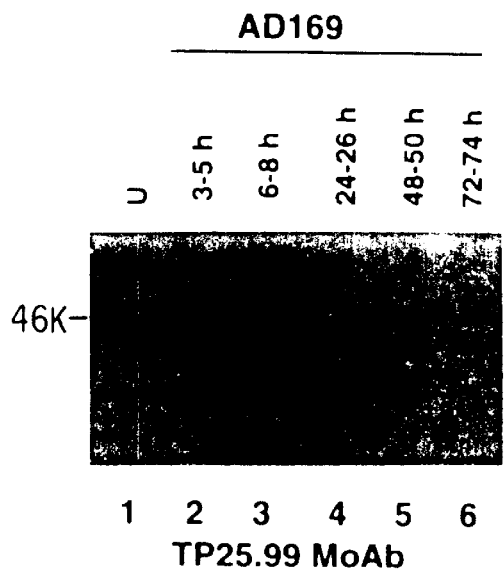

In the present invention, flow cytometry and immunofluorescence experiments confirmed that cell surface expression of class I heavy chains are greatly reduced at late times post-infection in HCMV wild-type strain AD169 infected HFF cells. Radiolabeling-immunoprecipitation experiments indicated that down-regulation of newly synthesized MHC class I heavy chains occurred throughout the course of infection, beginning at very early times (3 h) post-infection (FIG. 4C). This reduction has been reported to be at the post-translational level: class I heavy chains have a higher turnover rate in HCMV-infected cells than in uninfected cells (Beersma et al., 1993). Such instability of class I heavy chains results in a reduced cell-mediated immune response to HCMV infection since viral peptides will be inefficiently presented. Thus, the reduction in class I heavy chain expression is important in terms of evasion of a host's immune system in the establishment of persistent or latent infections by HCMV (Gooding, 1992).

A bank of HCMV mutants, which represent 18 ORFs which are dispensable for viral replication in tissue culture, were screened for their ability to cause down-regulation of MHC class I heavy chains. A 7-kb region of the S component of the HCMV genome, containing ORFs US2-US11 (bases 193119–200360), was clearly shown to contain genes which are required for this phenotype (data summarized in FIG. 9). Within this region, there are two subregions, each of which contain genes sufficient for heavy chain down-regulation.

Subregion A contains ORFs US2-US5 (bases 193119–195607). It has been proposed that US2 and US3 encode membrane glycoproteins (Chee et al., 1990). US3 is a differentially spliced gene which is expressed throughout the viral replicative cycle and encodes a protein with transcriptional transactivating function (Tenney and Colberg-Poley, 1991; Colberg-Poley et al., 1992; Tenney et al., 1993; Weston, 1988). Several smaller ORFs are also present in this subregion (between the ORFs US3 and US5), but their expression characteristics or functions have not been reported. Gretch and Stinski (1990) reported that there is a 1.0-kb early mRNA transcribed from this region of the HCMV genome, but it was not fine-mapped. Now, for the first time, it has been found that it is expression of the US2 gene which is sufficient for MHC class I down-regulation within this locus (US2-US5).

Figure 5A:
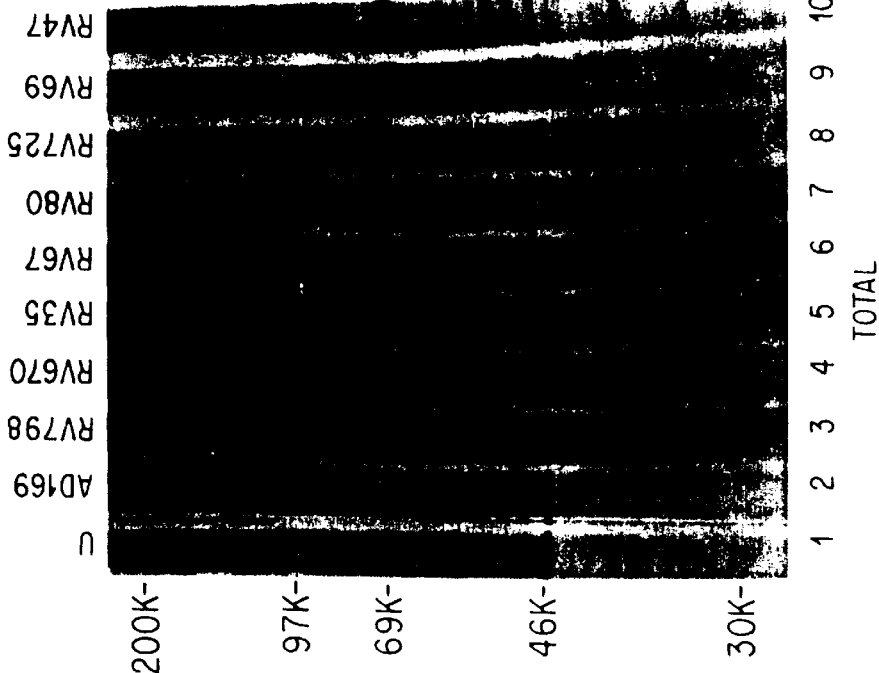
FIGS. 5A–5B show the analysis of heavy chain expression in cells infected with HCMV mutants. HFF cells were uninfected (U) or infected with the indicated virus (multiplicity of infection of 5 PFU/cell) and radiolabeled for 4 h at late times post-infection (69–73 h). Proteins were harvested immediately after radiolabeling.
Figure 15A:
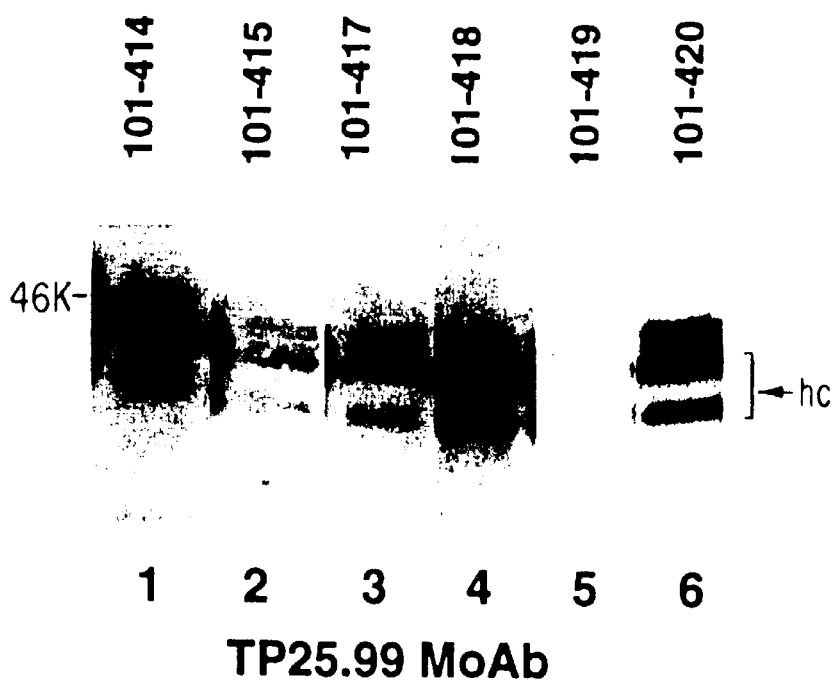
FIGS. 15A–15B are Western blots of cell lines expressing the HCMV US11 gene. Uninfected human U373-MG cells stably-transfected with a US11 expression plasmid were analyzed by Western Blot analysis for MHC class I heavy chain expression (FIG. 15A) and for US11 expression (FIG. 15B) using the TP25.99 monoclonal antibody and the US11 polyclonal antisera, respectively.
Figure 15B:
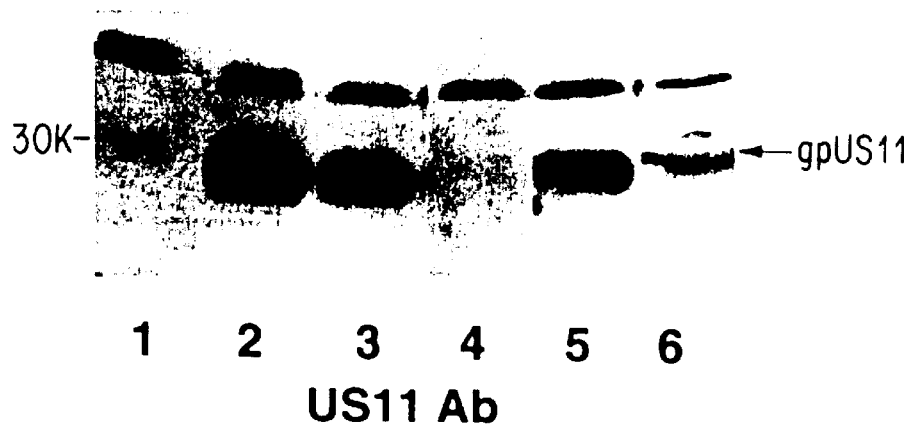

Subregion B, which is also sufficient for MHC class I heavy chain reduction, contains the US10 and US11 genes (FIG. 9), bases 199083–200360. However, based on data using HCMV mutant RV670 which expresses wild-type levels of the US10 gene product, US10 expression is not sufficient for down-regulation of heavy chain expression (FIG. 5A). The genetic data implicated the US11 gene product as being required. It is demonstrated herein that US11 expression is sufficient to cause MHC class I heavy chain down-regulation in stably-transfected uninfected cells in the absence of other HCMV proteins (FIG. 15). RNA and protein expression from US11 begins early and proceeds throughout the course of infection (Jones and Muzithras, 1991). US11 encodes a glycoprotein of 32-kDa (gpUS11) which has N-linked sugar residues that are endoglycosidase H sensitive. Immunofluorescence experiments show that gpUS11 is not present on the cell surface, but is detected in the cytoplasm of HCMV-infected cells (FIG. 10).

Thus, gpUS11 is retained in the endoplasmic reticulum or cis golgi. The characteristics of HCMV gpUS11 are similar to the 25-kDa glycoprotein (E3-19K) encoded from the E3 region of adenovirus type 2. Ad E3-19K is nonessential for viral replication. It has been shown to contain endoglycosidase H-sensitive N-linked sugar residues, be retained in the endoplasmic reticulum, and bind MHC class I heavy chains, thereby preventing their transport to the cell surface 9 (Anderson et al., 1985; Burgert and Kvist, 1985). In contrast to Ad E3-19K, a direct association between gpUS11 and class I heavy chains (i.e., by coimmunoprecipitation) was not detected (data not shown).

The identification of the US2-US11 gene region as the region of the HCMV genome required for down-regulation of MHC class I heavy chains is significant in several respects. As mentioned above, expression from this region of the genome throughout the course of infection acts to interfere with an effective cell mediated immune response. Surface expression of MHC class I molecules is required for antigen presentation to activate and expand cytotoxic T lymphocyte (CTL) precursors populations (Schwartz, 1985). In addition, they are further required for target recognition by the activated CTLs (Zinkernagel and Doherty, 1980). In MCMV, CTLs against the major immediate-early protein are protective against lethal infection by this virus (Jonjic et al., 1988). However, in HCMV-infected individuals, the frequency of CTLs against the analogous HCMV immediate-early protein, IE1, are reported to be extremely rare (Gilbert et al., 1993). Recent studies have shown that IE peptides are more efficiently presented by interferon-γ-treated HCMV-infected cells, than by untreated infected cells (Gilbert et al., 1993). Interferon γ causes increased surface expression of MHC class I proteins. Thus, increasing the expression of class I heavy chains in HCMV-infected cells may be important in the efficient generation of IE-specific CTLs, or CTLs against other important HCMV antigens. A HCMV mutant deleted of the US2-US11 gene region would have this effect since the class I heavy chains are not down-regulated when cells are infected with this mutant. Therefore, a deletion of this region of the viral genome is important in the development of a live HCMV vaccine to induce an effective anti-HCMV immune response.

The elucidation of the US2 and US11 gene products as being sufficient for class I down-regulation is significant for several reasons based on the fact that class I proteins mediate the activation of, and recognition of target cells by, cytotoxic T lymphocytes, the primary player in the cellular immune response. US2 and US11, as genes or, perhaps, as proteins, may be incorporated in clinical treatment strategies when expression of cellular MHC class I is undesirable: gene therapy vectors (e.g., adenovirus vectors) and to reduce allograft rejection. US2 and US11 can be used as tools to identify other cellular proteins which may interact with class I heavy chains and thereby effect class I heavy chain protein stability, processing, and transport to the cell surface. In an HCMV vaccine strategy using a live virus, removal of US2, or US11, or both may yield a virus which is a better immunogen than a virus which contains these genes.

Several years ago it was reported that the HCMV UL18 ORF encoded a protein which resembled MHC class I heavy chains (Beck and Barrell, 1988). It was hypothesized that the down-regulation of heavy chains in HCMV-infected cells was due to competition of the UL18 gene product for β2-microglobulin, which effectively prevented the normal association of class I heavy chains and β2-microglobulin (Browne et al., 1990). This hypothesis was essentially dispelled when a HCMV mutant deleted of UL18 retained its ability to down-regulate heavy chain expression (Browne et al., 1992). It remained possible that the UL18 gene product was only one of several HCMV genes whose expression is sufficient for this phenotype. However, the present invention data indicates that only genes within the US2-US11 region are sufficient for class I heavy chain down-regulation.

The existence of two independent mechanisms which result in down-regulation of MHC class I expression emphasizes the importance of this phenotype for successful infection and persistence in the host. One mechanism may serve as a backup system for the other, but it is also plausible that there is cell type specificity for each system. Such a situation exists with herpes simplex virus. It was recently reported that the 88 amino acid US12 gene product (ICP47) is sufficient for class I heavy chain sequestering in the endoplasmic reticulum (York et al., 1994). However, expression of heavy chains is not affected in herpes simplex virus-infected mouse cells, although ICP47 is expressed in those cells and murine heavy chains are down-regulated when expressed in an HSV-infected human fibroblast system (York et al., 1994).

A pharmaceutical composition may be prepared containing the recombinant HCMV mutant of the present invention in which the region of the HCMV genome capable of down-regulating MHC Class I expression in infected cells has been deleted. The deleted region of the HCMV genome is preferably open reading frame US2, US11, or both. A stabilizer or other appropriate vehicle may be utilized in the pharmaceutical composition.

As discussed earlier, the recombinant HCMV mutant of the present invention from which a region of the HCMV genome capable of down-regulating MHC class I expression has been deleted, may be used in a vaccine for the prevention of cytomegalovirus infections. The deleted region of the HCMV genome is preferably open reading frame US2, US11, or both. The vaccine comprises an effective amount of the recombinant HCMV mutant in a pharmaceutically acceptable vehicle. An adjuvant may be optionally added to the vaccine.

A method of immunizing an individual against cytomegalovirus may be carried out by administering to the individual an immunogenic amount of the recombinant HCMV mutant of the present invention which is devoid of the gene sequence capable of down-regulating MHC class I expression. The gene sequence which has been deleted is preferably the region containing open reading frame US2, US11, or both.

A method of preventing or reducing susceptibility in an individual to acute cytomegalovirus may be carried out by administering to the individual an immunogenic amount of the recombinant HCMV mutant of the present invention which is devoid of the gene sequence capable of down-regulating MHC class I expression. The gene sequence which has been deleted is preferably the region containing open reading frame US2, US11, or both.

Down-regulation of MHC class I expression in a cytomegalovirus infected cell may be controlled by a method having the steps of identifying a gene sequence capable of down-regulating the major histocompatibility complex and deleting the identified gene sequence from the cytomegalovirus genome.

As discussed earlier, the gene sequence involved in the MHC class I heavy chain down-regulation can be incorporated into adenovirus vectors or similar virus-based gene therapy vectors to minimize the immune response and allow the use of the vectors in gene therapy. One virus-based gene therapy vector comprises the gene sequence of the open reading frame of US2. Another virus-based gene therapy vector comprises the gene sequence of the open reading frame of US11. Another virus-based gene therapy vector comprises the gene sequences of subregions A and B (open reading frames US2-US5 and US10-US11, respectively).

EXAMPLE 1

Virus and Cells

HCMV strain AD169 is obtained from the American Type Culture Collection and propagated according to standard protocols known by those skilled in the art. Human foreskin fibroblast (HFF) cells were isolated in this laboratory and used below passage twenty (Jones and Muzithras, 1991). They were grown in Dulbeccos modified Eagle medium (DMEM) containing 10% fetal bovine serum and 25 mM HEPES.

DNA Sequence

The numbering system of Chee et al. (1990) of the HCMV strain AD169 DNA sequence (Genbank accession number X17403) is used in the present invention.

Plasmids

Plasmids used for creation of HCMV mutants were constructed using the method described previously (Jones et al., 1991; Jones and Muzithras; 1992). Generally, the β-glucuronidase reporter gene is surrounded on each side by 1.5-kb of HCMV sequences which flank the gene(s) to be deleted from the virus. In each case, the plasmid DNA is linearized with a restriction enzyme which cuts within the prokaryotic backbone prior to transfection. The HCMV strain AD169 genomic DNA fragments are derived from either pHind-G, pHind-X, or pXba-P which contain the HindIII-G (bases 176844 to 195837), -X (bases 195837 to 200856), and XbaI-P (bases 200391 to 206314) DNA fragments, respectively (Oram et al., 1982; Jones et al., 1991). pUS7/US3 contained the 1.7-kb PstI-PstI HCMV fragment (bases 196447 to 194741 in pIBI30 vector [International Biotechnologies, Inc.]) derived from pHind-G and pHind-X.

Replacement of ORFs IRS1 through US9 and US11 (but not US10) by β-glucuronidase and plasmid vector sequences (i.e., RV670) was described previously (Jones amd Muzithras, 1992).

Figure 1A:
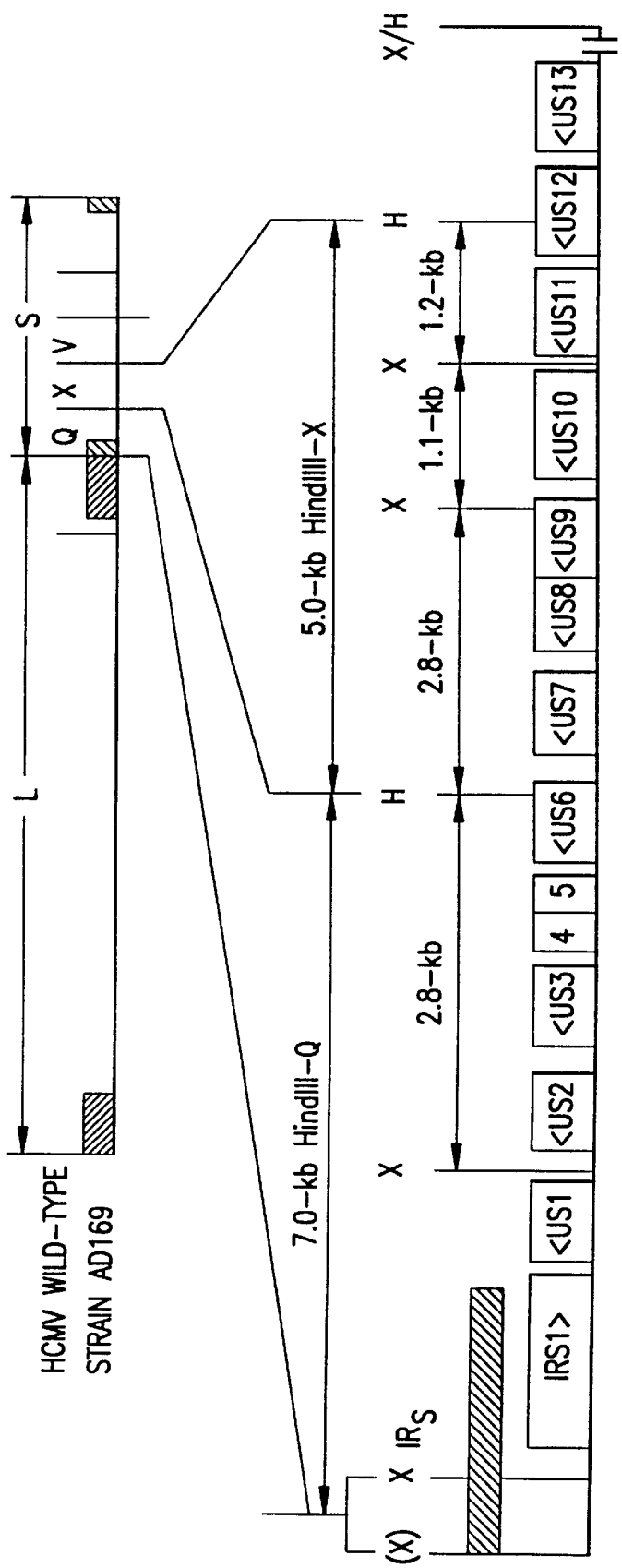
Figure 1B:
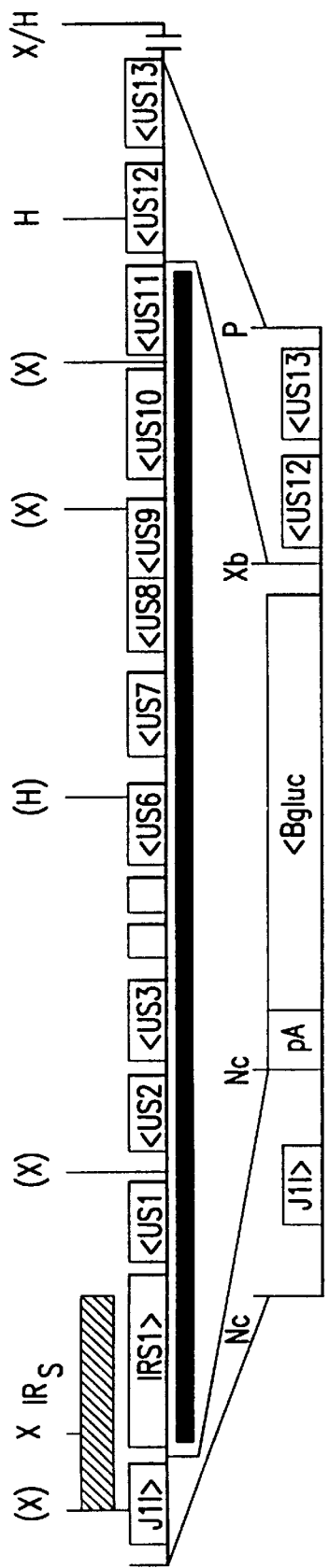

To replace HCMV ORFs US11 through IRS1 by β-glucuronidase (i.e., RV7186; FIG. 1B), pBgdUS11/IRS1 was constructed. Sequentially, this plasmid contained the 1.8-kb fragment PstI-XbaI fragment (bases 202207 to 200391, containing US13, US12, and US11 promoter sequences, from pXba-P), β-glucuronidase, a 288-b SV40 fragment containing the early and late polyadenylation signals (from pRcCMV [Invitrogen]), and the 1.7-kb NcoI-NcoI fragment (bases 189763 to 188062, containing J11 to IRL1 sequences, from pHind-G).

Figure 1C:
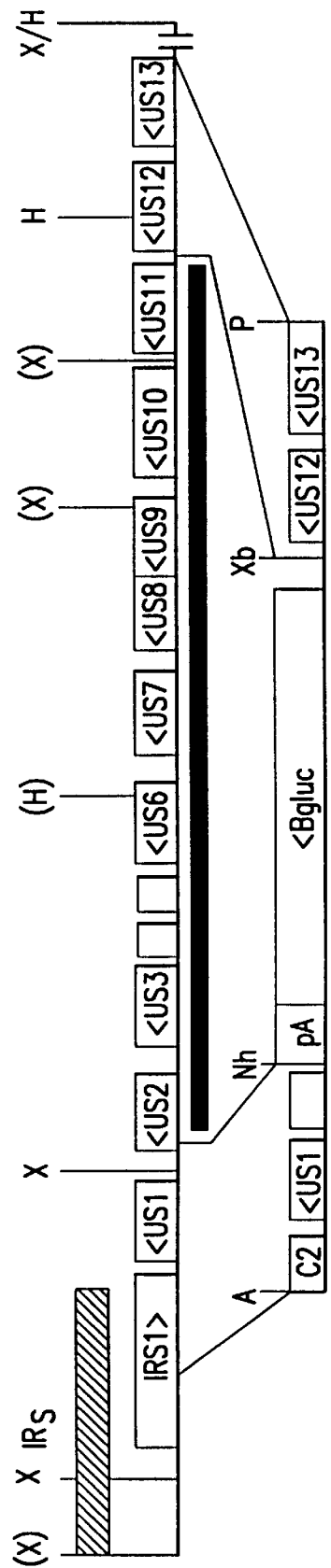

To replace HCMV ORFs US11 through US2 by β-glucuronidase (i.e., RV798; FIG. 1C), pBgdUS11/US2 was constructed. Sequentially, this plasmid contained the 1.8-kb fragment PstI-XbaI fragment (bases 202207 to 200391, containing US13, US12, and US11 promoter sequences, from pXba-P), β-glucuronidase, a 255-b fragment containing the US10 polyadenylation signal (bases 199276 to 199021, from pHind-X), and the 1.3-kb NheI-ApaI fragment (bases 193360 to 192033, containing C-terminal US2 to IRS1 sequences, from pHind-G).

Figure 1D:
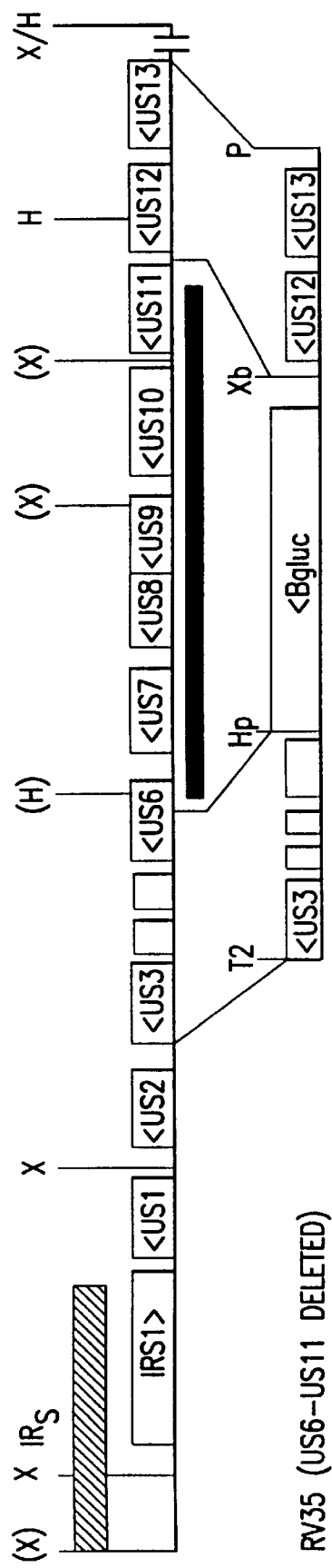

To replace HCMV ORFs US11 through US6 by β-glucuronidase (i.e., RV35; FIG. 1D), pBgdUS11/US6 was constructed. Sequentially, this plasmid contained the 1.8-kb PstI-XbaI fragment (bases 202207 to 200391, containing US13, US12, and US11 promoter sequences, from pXba-P), β-glucuronidase, and the 1.5-kb HpaI-SstII fragment (bases 195589 to 194062, containing C-terminal US6 to US3 sequences, from pHind-G).

Replacement of HCMV ORFs US11-US10, or ORF US11 (singly), by β-glucuronidase (i.e., RV67 and RV699, respectively) were described previously (Jones et al., 1991). In addition, replacement of HCMV ORFs US9-US8, US7 (singly), or US6 (singly), by β-glucuronidase (i.e., RV80, RV725, and RV69, respectively) were described previously (Jones and Muzithras, 1992).

Figure 1E:
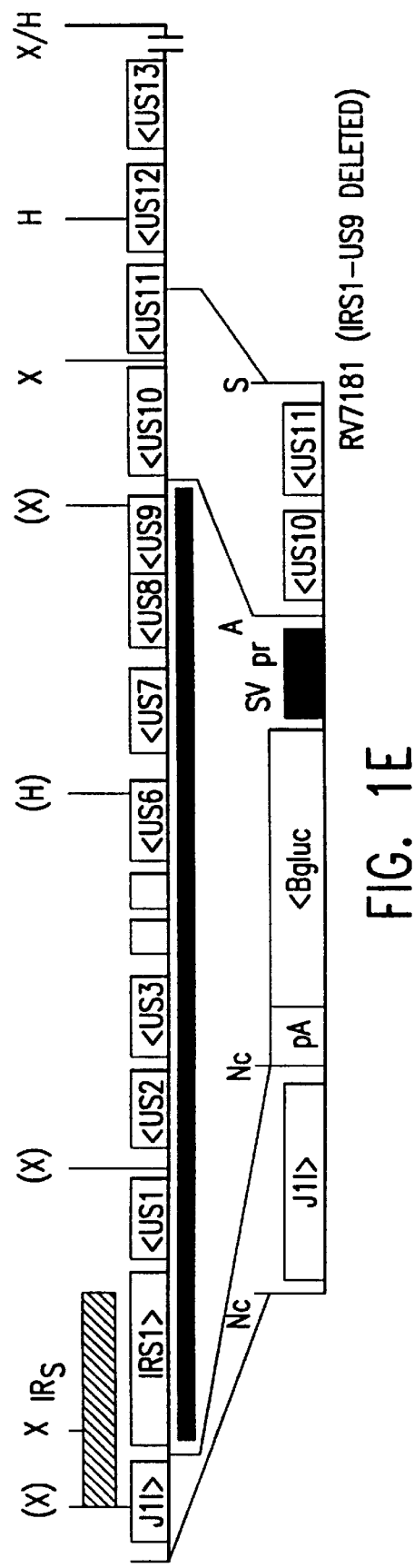

To replace HCMV ORFs US9 through IRS1 by μ-glucuronidase (i.e. RV7181; FIG. 1E), pBgdUS9/IRS1 was constructed. Sequentially, this plasmid contained the 1.1-kb SalI-ApaI fragment (bases 200171 to 199021), the 351-b SV40 early promoter (from pRcCMV), β-glucuronidase, the 288-b SV40 polyadenylation signal fragment, and the 1.7-kb NcoI-NcoI fragment (bases 189763 to 188062, containing J11 to IRL1 sequences, from pHind-G).

To replace HCMV ORFs US6 through IRS1 by β-glucuronidase (i.e., RV7177; FIG. 1F), pBgdUS6/IRS1 was constructed. Sequentially, this plasmid contained the 1.7-kb NcoI-NcoI fragment (bases 188062 to 189763, containing IRL1, J11, and IRS1 promoter sequences, from pHind-G), β-glucuronidase, the 255-b fragment containing the US10 polyadenylation signal (bases 199276 to 199021, from pHind-X), and the 1.8-kb BsmI-SauI fragment (bases 196222 to 198030, containing US7 to C-terminal US9 sequences, from pHind-X).

To replace HCMV ORFs US3 and US2 by β-glucuronidase (i.e., RV47; FIG. 1G), pBgdUS3/US2 was constructed. Sequentially, this plasmid contained the 1.7-kb PstI-PstI fragment (bases 196447 to 194741), a 180-b SmaI-HaeIII fragment containing the HSV-1 gH promoter (McKnight, 1980), β-glucuronidase, the 255-b US10 polyadenylation signal fragment, and the 1.3-kb NheI-ApaI fragment (bases 193360 to 192033, containing C-terminal US2 to IRS1 sequences, from pHind-G).

To replace HCMV ORF US1 by β-glucuronidase (i.e., RV5122; FIG. 1H), pBgdUS1 was constructed. Sequentially, this plasmid contained the 1.8-kb AatII-SstI fragment (bases 190884 to 192648, containing IRS1 and US1 C-terminal sequences, from pHind-G), a 180-b SmaI-HaeII fragment containing the HSV-1 gH promoter (McKnight, 1980), β-glucuronidase, the 255-b US10 polyadenylation signal fragment, and the 1.6-kb SphI-SphI fragment (bases 192934 to 194544, containing US2 and C-terminal US3 sequences, from pHind-G).

To replace HCMV ORF IRS1 by β-glucuronidase (i.e., RV46; FIG. 1I), pBgdIRS1 was constructed. Sequentially, this plasmid contained the 1.7-kb NcoI-NcoI fragment (bases 188062 to 189763, containing IRL1, J11, and IRS1 promoter sequences, from pHind-G), β-glucuronidase, the 255-b fragment containing the US10 polyadenylation signal (bases 199276 to 199021, from pHind-X), and the 1.2-kb NarI-XhoI fragment (bases 191830 to 193003, containing C-terminal IRS1 and US1 sequences, from pHind-G).

Figure 1J:
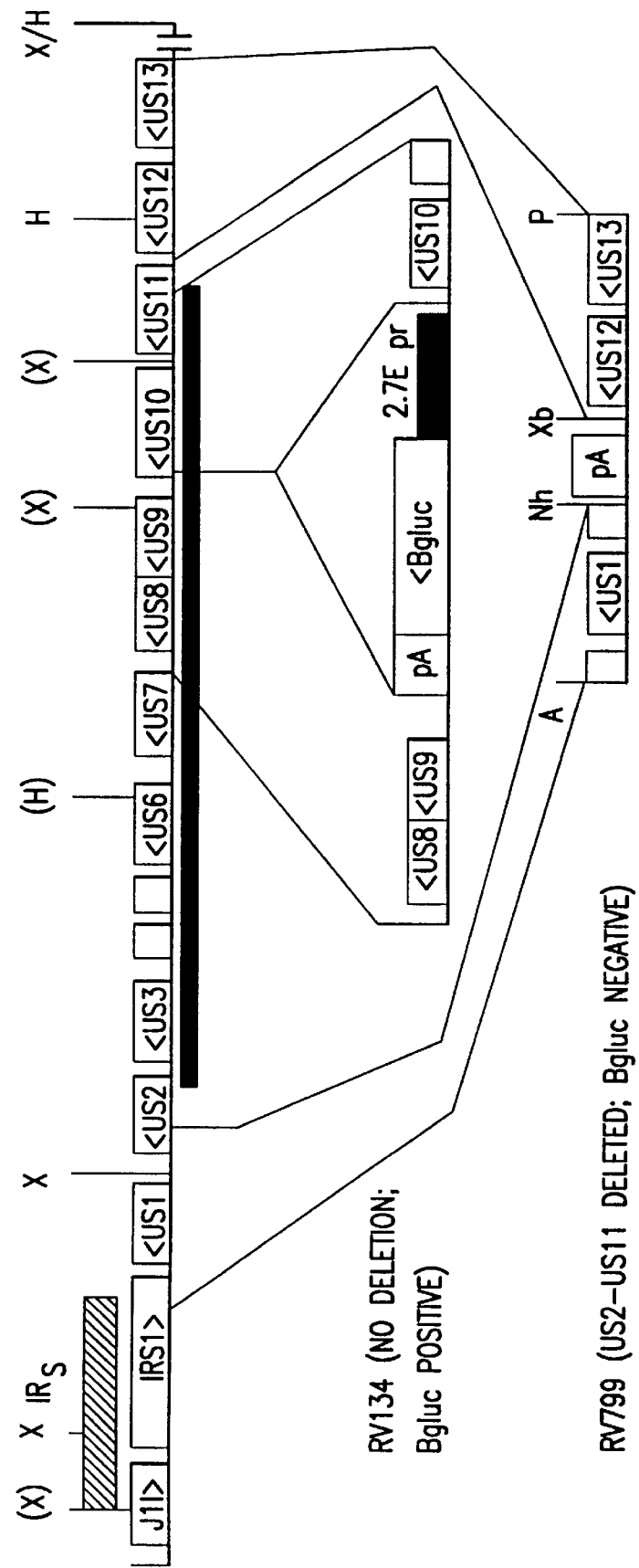

To delete HCMV ORFs US11 through US2 without insertion of a reporter gene (i.e., RV799; FIG. 1J), pdUS11/US2 was constructed. Sequentially, this plasmid contained the 1.8-kb fragment PstI-XbaI fragment (bases 202207 to 200391, containing US13, US12, and US11 promoter sequences, from pXba-P), β-glucuronidase, 65-b NruI-ApaI fragment containing the US10 polyadenylation signal (bases 199086 to 199021, from pHind-X), and the 1.3-kb NheI-ApaI fragment (bases 193360 to 192033, containing C-terminal US2 to IRS1 sequences, from pHind-G).

Figure 2A:
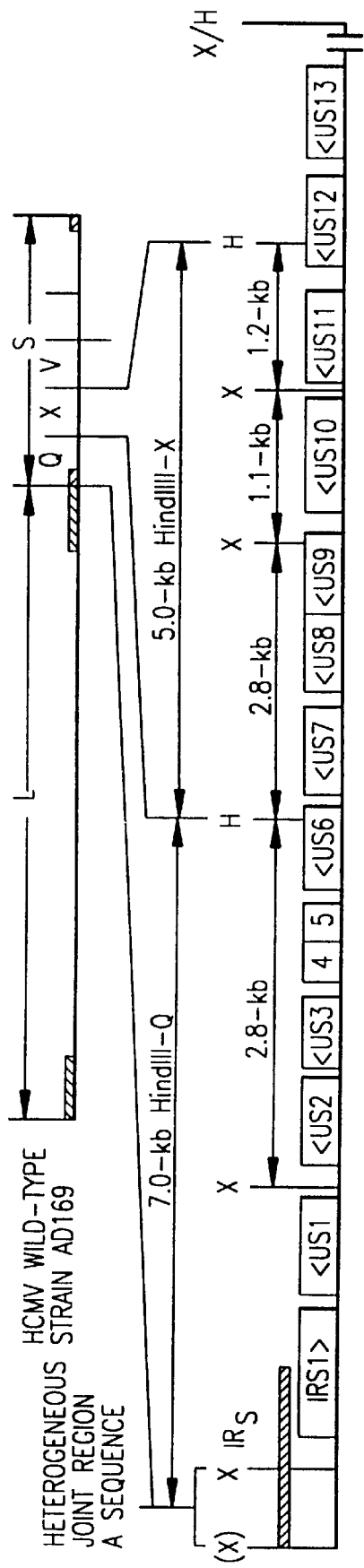
Figure 3A:
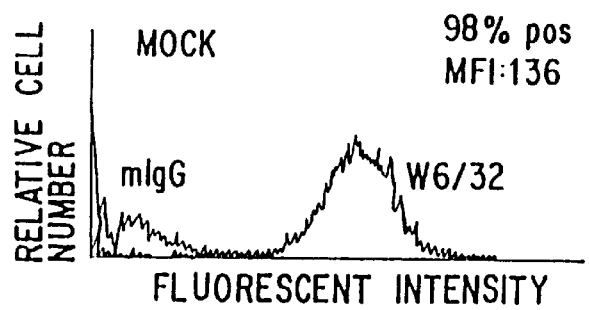
FIGS. 3A–3E show the detection of cell surface MHC class I by immunofluorescence-flow cytometry in HCMV-infected cells. Human foreskin fibroblast (HFF) cells were infected with the indicated virus at a multiplicity of infection of 5 PFU/cell for 72 h. At that time, cells were fixed in 1% paraformaldehyde and stained with primary antibody specific for HLA-A, -B, -C (W6/32) or control mouse IgG (isotype matched) followed by secondary FITC-conjugated goat anti-mouse IgG. Percent positive cells ($5 \times 10^3$ total) and mean fluorescent intensity (MFI) were calculated on the basis of forward angle light scatter versus log-integrated 90° light scatter using the Immuno Program, Coulter MDADS I.
Figure 3B:
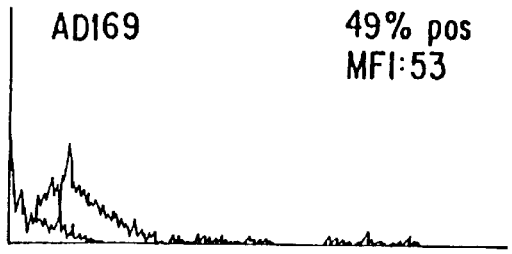
Figure 3C:
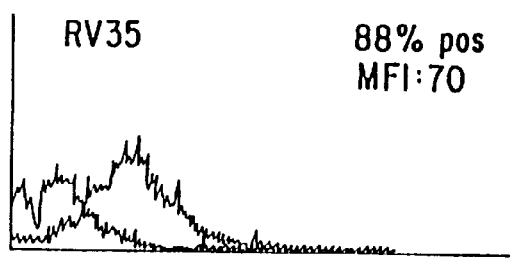
Figure 3D:
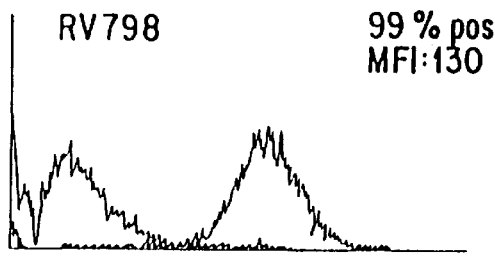
Figure 3E:
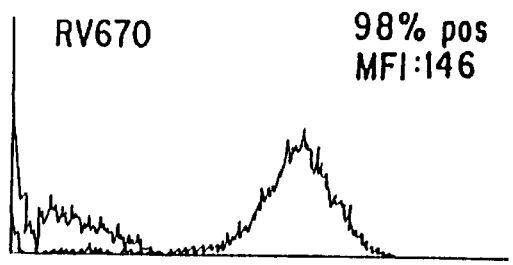

To replace HCMV ORFs US11 through US4 by β-glucuronidase (i.e., RV8146; FIG. 2B), pBgΔUS11/US4 was constructed. Sequentially, this plasmid contains the 1.8-kb fragment PstI-XbaI fragment (bases 202207 to 200391; containing US13, US12, and US11 promoter sequences; from pXba-P), β-glucuronidase, the 180-b SmaI-HaeIII fragment containing the HSV-1 thymidine kinase polyadenylation signal (McKnight, 1980), and the 1.662-kb EcoRV-SmaI (bases 195083 to 193421; containing US3 and US2 sequences; from pHind-G).

To replace HCMV ORFs US11 through US3 by β-glucuronidase (i.e., RV8173; FIG. 2C), pBgΔUS11/US3 was constructed. Sequentially, this plasmid contains the 1.8-kb fragment PstI-XbaI fragment (bases 202207 to 200391; containing US13, US12, and US11 promoter sequences; from pXba-P), β-glucuronidase, the 180-b SmaI-HaeIII fragment containing the HSV-1 thymidine kinase polyadenylation signal (McKnight, 1980), and the 1.464-kb KpnI-SacI (bases 194112 to 192648; containing US2 and US1 sequences; from pHind-G).

Isolation of Recombinant Mutant HCMV

Creation and isolation of recombinant mutant HCMV was done as described previously (Jones et al., 1991; Jones and Muzithras, 1992). HFF cells were split so that they were 70–80% confluent on the day of transfection. The cells were trypsinized and suspended to $5.6 \times 10^5$ cells per ml in DMEM/10% FCS/25 mM HEPES. The DNA was transfected using a modified calcium phosphate co-precipitation technique. 1.5 μg of infectious HCMV DNA and 2.5 μg of linearized plasmid DNA were mixed in the calcium chloride solution (300 μl containing 10 mM Tris pH 7.0/250 mM calcium chloride) and chilled on ice. To initiate the co-precipitation, the DNA was removed from the ice and 300 μl 2X HeBS pH 6.95 (at room temperature; 1X HeBS was 19.2 mM HEPES, 137 mM NaCl, 5 mM KCl, 0.8 mM sodium phosphate, 0.1% dextrose) was added dropwise with gentle mixing. After 1.5 minutes, the precipitate was placed on ice (to prevent further precipitate from forming). The precipitate was mixed with $3 \times 10^6$ cells (in suspension) and placed in a 82 mm tissue culture plate. After 6 h at 37° C., the media was removed and the cells were shocked with 20% DMSO in 1X HeBS for 2 minutes. The cells were washed twice with PBS and growth media was added. The media was changed every 4–7 days. After 14 days, viral plaques were observed and the cells were overlaid with 0.5% agarose in DMEM containing 150 μg/ml X-gluc (5-bromo 4-chloro 3-indol 1-glucuronide; Biosynth). Blue plaques (i.e., β-glucuronidase-positive mutant virus plaques) were picked several days after adding the overlay. Recombinant viruses were plaque purified three times. HCMV mutant RV799 was β-glucuronidase-negative and was isolated using a modification of the above procedure. In this case, β-glucuronidase-positive HCMV mutant RV134 was the parent virus (Jones et al., 1991). Thus, RV134 genomic DNA was used instead of wild-type strain AD169 DNA in the transfections. Primary plaques appearing on the primary transfection plates were picked at random and replated on HFF cells. After 10 days, the media was removed and the infected cells were overlaid with X-gluc-containing agarose as described above. In this case, white plaques (β-glucuronidase-negative mutant virus plaques) were picked 4 days later and plaque purified. The proper genomic organization of each of the HCMV mutants was verified by DNA blot hybridization analysis as described previously (Jones et al., 1991).

Antibodies

Rabbit polyclonal antisera reactive with HCMV US11 proteins and HCMV UL80 proteins are described previously (Jones et al., 1991; 1994). Murine monoclonal antibodies W6/32, specific for a conformation-dependent epitope on the heavy chain of human MHC class I proteins, and Ber-T9, specific for the human transferrin receptor, were purchased. Murine monoclonal antibody TP25.99 (D'Urso et al., 1991), specific for a conformation-independent epitope on the heavy chain of human MHC class I proteins, was obtained from Dr. S. Ferrone (Department of Microbiology, New York Medical College, Valhalla, N.Y.). Murine monoclonal antibody 9221, specific for the HCMV IE1 protein, was purchased from Dupont.

US2 polyclonal antisera was obtained by isolating a US2-glutathione S-transferase fusion (GST) protein which was subsequently used as the immunogen in rabbits. Specifically, the portion of the HCMV US2 gene encoding amino acids 20 through 110 was generated by polymerase chain reaction as a NcoI/EcoRI fragment and fused in frame with the C-terminus of the GST protein in the pGST(Nco) vector to yield the plasmid pGST(Nco)-US2. The vector pGST(Nco) was modified from the glutathione S-transferase fusion vector pGEX-2T (Pharmacia stock no. 27-4801-01) by digestion with SmaI and the addition of NcoI linkers such that the open reading frame was retained. The plasmid PGST(Nco)-US2 was introduced into $E.\ coli$ strain DH5 and fusion protein synthesis was induced with IPTG. The GST-US2 fusion protein was isolated from sonicated $E.\ coli$ by binding to and elution from glutathione sepharose 4B (Pharmacia) as described by the manufacturer. One hundred microgram aliquots of the GST-US2 fusion protein were used as an immunogen in female New Zealand white rabbits to generate US2 polyclonal antisera.

Radiolabeling and Immunoprecipitation of Infected Cell Proteins

Pulse-chase radiolabeling was done according to standard protocol (Sambrook et al., 1989). HCMV-infected HFF cells (multiplicity of infection equalled five) was pulse-labeled with 200 μCi of [$^{35}$S] methionine and [$^{35}$S]cysteine (NEN-DuPont) per ml in methionine/cysteine-free Dulbecco's modified Eagle medium (DMEM) at the indicated time period post-infection. The radioactive media was removed, the cells washed twice in complete DMEM, and chases were done for the indicated time in complete DMEM. Proteins were extracted using triple detergent lysis buffer (Sambrook et al., 1989). The cleared protein extracts (supernatant after centrifugation for 5 minutes at 15000×g and 4° C.) were retained for immunoprecipitation according to standard protocol (Sambrook et al., 1989). Proteins binding to antibodies were pelleted using protein A sepharose (Pharmacia). For immunoprecipitations of the human transferrin receptor, rabbit anti-mouse IgG (Pierce) were added prior to protein A sepharose. The washed immunoprecipitates were boiled in the presence of 2-mercaptoethanol and electrophoresed in denaturing polyacrylamide gels. The gels were fixed and soaked in 1M sodium salicylate fluor (Sambrook et al., 1989) prior to drying and autoradiography.

Immunofluorescence

Immunofluorescence assays were done according to standard protocol (Harlow, 1989). All procedures were done in 60 mm tissue culture plates. Briefly, infected or uninfected HFF cells were fixed with 4% paraformaldehyde and permeabilized with 0.2% Triton X-100 (where indicated). After adding 3% bovine serum albumin in phosphate-buffered saline, the cells were held overnight at 4° C. The cells were treated sequentially with the following antisera, each for 30 minutes at room temperature: 10% HCMV-negative human serum (to block any Fc receptors); the indicated primary antibody; and FITC-conjugated anti-mouse or anti-rabbit IgG, as appropriate.

EXAMPLE 2

Class I Down-Regulation in HCMV-Infected Human Fibroblasts

Figure 4B:
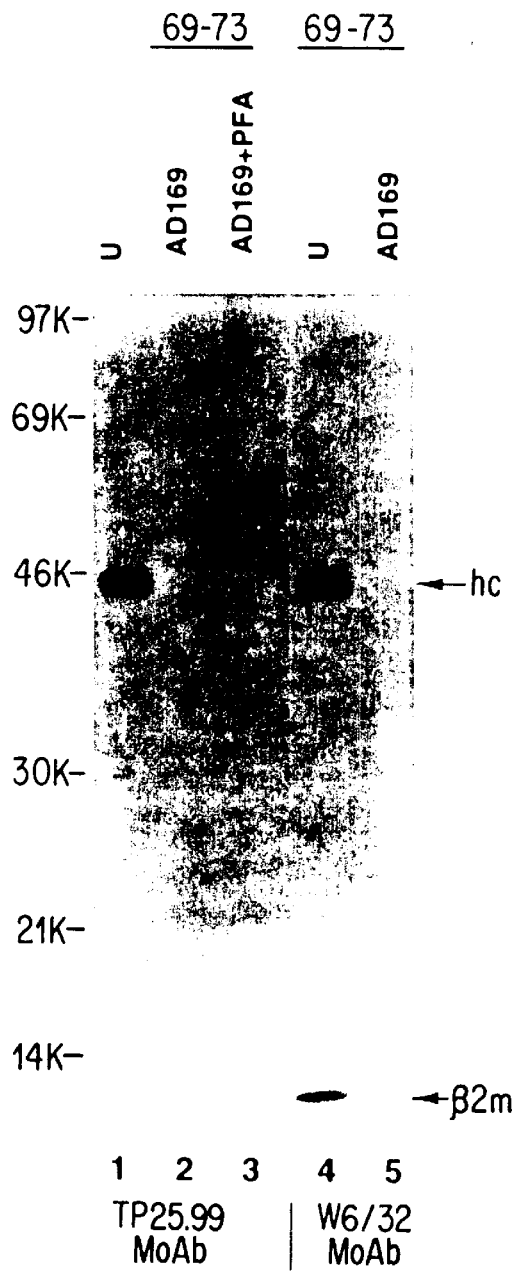

The timing and nature of MHC class I heavy chain down-regulation was ascertained in the human foreskin fibroblast (HFF) cell culture system. By flow cytometry, HCMV strain AD169 wild-type-infected HFF cells were significantly reduced in the expression of class I heavy chains on their cell surface at late times post-infection (i.e., 72 h) using the conformation-dependent class I monoclonal antibody W6/32 (FIG. 3). In Western analyses using the conformation-independent class I monoclonal antibody (TP25.99), it was demonstrated that the steady state level of class I protein was also reduced at late times post-infection (FIG. 4A). Because viral peptides are presented at the cell surface by class I complexes assembled after infection, the status of class I proteins synthesized at various times post-infection was assessed by immunoprecipitation of metabolically radiolabeled proteins. As shown in FIG. 4B, reduction in expression of class I heavy chains was detected both in the presence and absence of the viral DNA synthesis inhibitor, phosphonoformate. This indicated that viral immediate-early or early gene functions are sufficient for heavy chain reduction. In addition, it was demonstrated that heavy chain down-regulation was detected at very early times post-infection: 3 h (FIG. 4C). Since this effect was observed using the conformation-independent antibody, the reduction reflects overall levels of newly synthesized heavy chains.

Screening of HCMV Mutants for the Loss of MHC Class I Down-Regulation

Figure 5B:
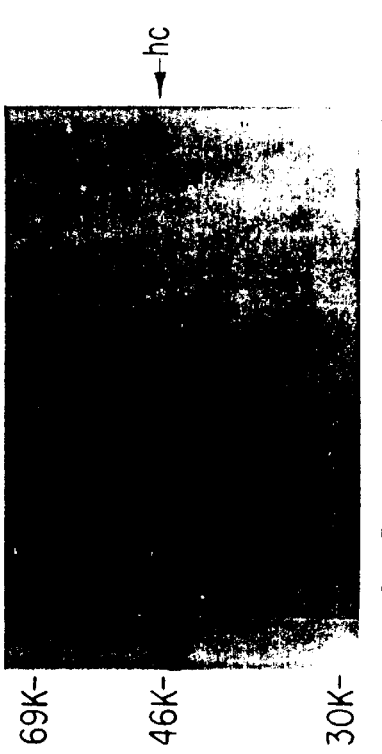
Figure 5C:
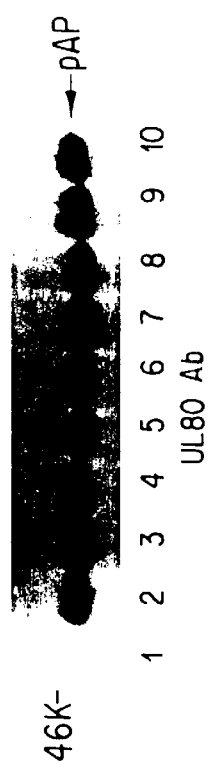
FIG. 5C is a radiograph to verify equal progression through the viral replicative cycle. UL80 proteins were immunoprecipitated using anti-assembly protein rabbit polyclonal antiserum.

Several previously constructed HCMV deletion mutants, representing 18 nonessential ORFs (UL33, UL81, IRS1, US1-US13, US27-US28, and TRS1), were screened for heavy chain expression by flow cytometry and immunoprecipitation analyses. Only RV670, a mutant deleted of a 9-kb region within the S component of the HCMV genome (Jones and Muzithras, 1992), did not retain the wild-type down-regulation phenotype (FIG. 5A). This mutant was deleted of at least 11 ORFs, IRS1 through US11 (except for US10), which includes the US6 family of genes (US6-US11) which putatively encode glycoproteins (Chee et al., 1990). To confirm this observation, two additional independently derived mutants which had the same deletion as RV670 and a new mutant, RV7186, deleted of the entire IRS1-US11 region (FIG. 1) were tested. Each was phenotypically identical to RV670 and stably expressed class I heavy chains. Previously, we constructed HCMV mutants deleted of US6 family ORFs, either individually or in groups (Jones and Muzithras, 1992), and similar deletion mutants within the adjacent IRS1-US3 region. By immunoprecipitation using the conformation-independent antibody, all of these mutants were shown to retain the ability to down-regulate class I heavy chains (FIG. 5A) at late times post-infection in HFF cells. Control experiments indicated that radiolabeling was equivalent between the different infected cell cultures (FIG. 5B) and that infection proceeded to late times equally, as judged by pp65 (FIG. 5B) and UL80 protein (FIG. 5C) expression. These data indicated: (i) that more than one viral gene is sufficient for the reduction in class I heavy chains; or (ii) gene(s) between US3 and US6, deleted in RV670 and RV7186 but not the other mutants, is required for the phenotype.

Identification of a 7-kb Region of the HCMV Genome Required for MHC Class I Down-Regulation To further localize the region containing gene(s) involved in MHC class I heavy chain down-regulation, additional HCMV replacement mutants containing deletions of multiple genes within the IRS1-US11 gene region were created (FIG. 1). One of these mutants, RV798, was deleted of genes from US2-US11. In HFF cells infected by RV798 and analyzed at late times post-infection, MHC class I heavy chains were not down-regulated as they are in wild-type strain AD169-infected cells (FIG. 5A); in fact, a slight stimulation is observed. Several independently-derived deletion mutants identical to RV798 were examined similarly: all lacked the ability to down-regulate class I heavy chains.

Figure 6A:
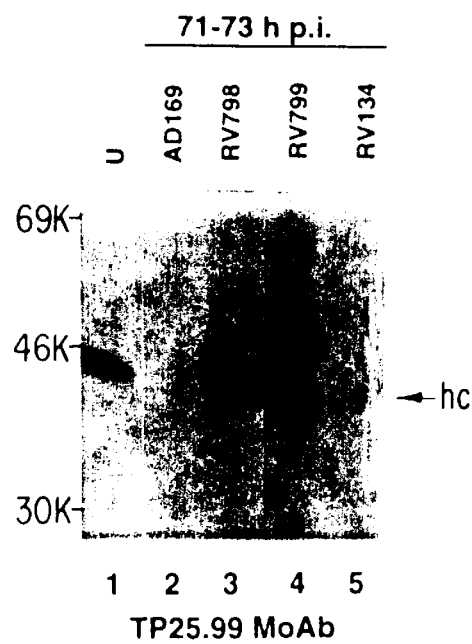
FIGS. 6A–6C show immunoprecipitation of class I heavy chains from RV798-, RV799-, RV134-, or AD169 wild-type-infected cells. HFF cells were uninfected (U) or infected with the indicated virus (multiplicity of infection of 5 PFU/cell) and radiolabeled for 2 h at late times post-infection (71–73 h). Proteins were harvested immediately after radiolabeling.
Figure 6B:
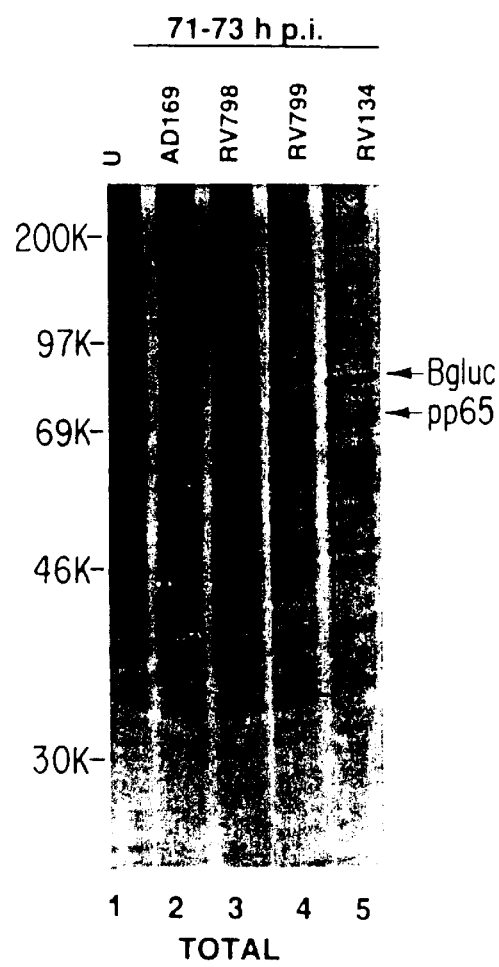
Figure 6C:
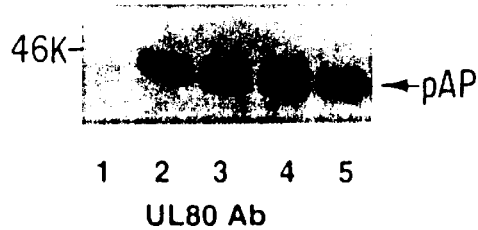

To further confirm that the 7-kb HCMV US2-US11 region contained the gene(s) required for heavy chain down-regulation, mutant RV799 was constructed which had the identical US2-US11 deletion as RV798, but was created by a different strategy. RV798 was derived from wild-type strain AD169 by inserting a β-glucuronidase marker gene in the place of US2-US11. In contrast, the parent of RV799 was RV134, a mutant which was β-glucuronidase-positive since it had a β-glucuronidase expression cassette inserted within the US9-US10 intergenic region (Jones et al., 1991). To create RV799, a plasmid was designed which upon recombination with the RV134 genome would simultaneously delete US2-US11 and the β-glucuronidase expression cassette (FIG. 1J). The proper RV799 HCMV mutant was isolated as a white plaque in the presence of the β-glucuronidase substrate, since it was β-glucuronidase-negative. RV799, but not the RV134 parent, was phenotypically identical to RV798 (FIG. 6). Thus, since RV798 and RV799 were created by different strategies from parents which retained the ability to down-regulate MHC class I heavy chains, this confirms that the gene(s) required for the phenotype are located within the 7-kb US2-US11 region (bases 193119–200360).

Figure 7:
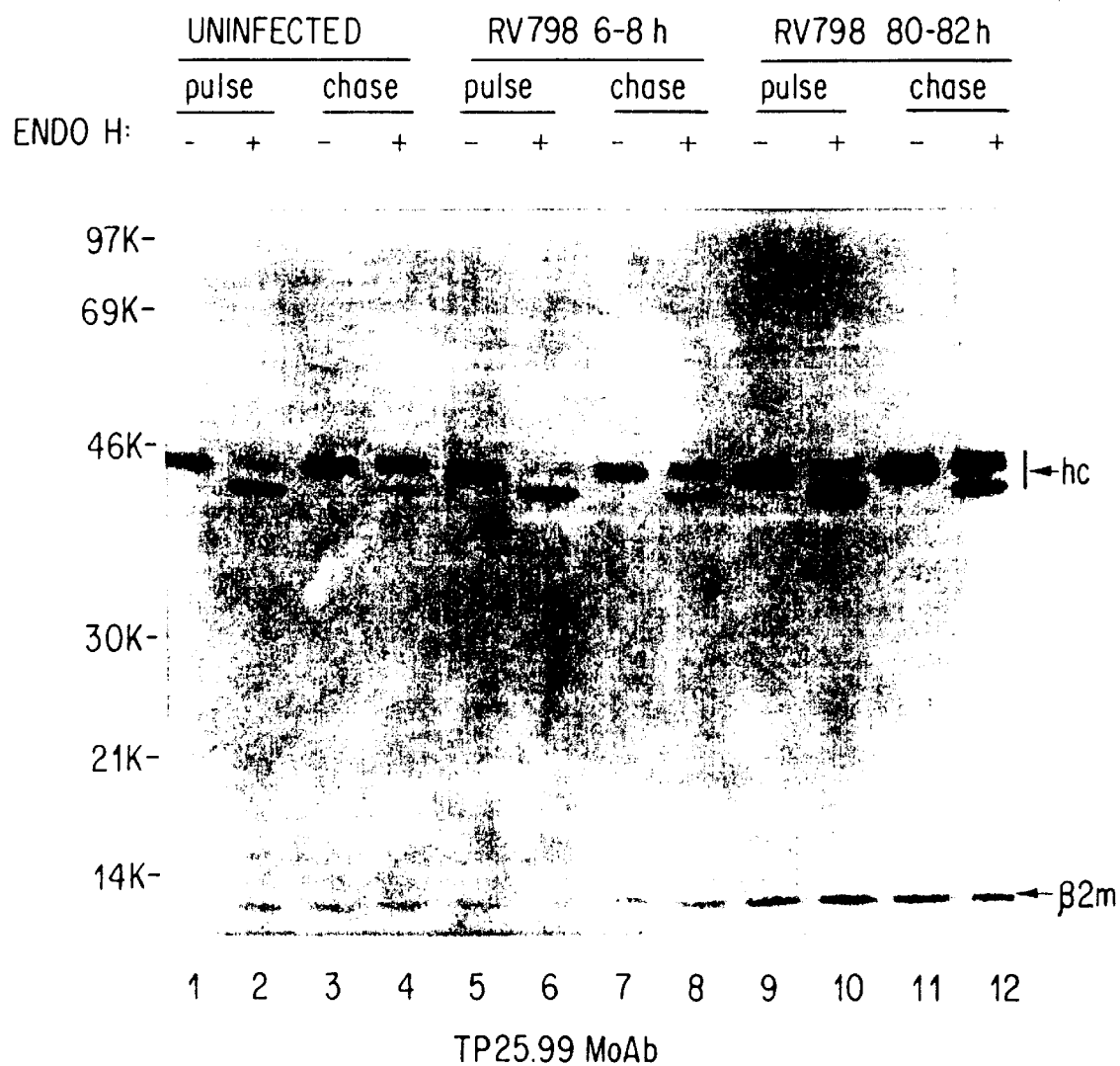
FIG. 7 is a radiograph showing the endoglycosidase H sensitivity of class I heavy chains synthesized in RV798-infected cells. HFF cells were infected with RV798 (multiplicity of infection of 5 PFU/cell) and radiolabeled for 2 h at early times (6–8 h) or late times (80–82 h) post-infection. For comparison purposes, uninfected cells were radiolabeled for 2 h. Proteins were harvested either immediately after radiolabeling (pulse) or after a 2 h chase (chase) in complete unlabeled media. Class I heavy chains were immunoprecipitated using TP25.99 murine monoclonal antibody. Immunoprecipitated protein were incubated for 6 h either in the presence (+) or absence (−) of 1.5 mU of endoglycosidase H, prior to SDS-polyacrylamide gel electrophoresis and fluorography.

To determine whether the proper surface expression of class I heavy chains occurred at late times post-infection with either RV798 or RV799, immunofluorescence assays were done. Using either the conformation-dependent (W6/32) or conformation-independent (TP25.99) monoclonal antibodies, surface expression of MHC class I heavy chains was detected in uninfected and RV798-and RV799-infected HFF cells, but not wild-type AD169-infected HFF cells. Proper maturation of class I heavy chains in uninfected cells yielded endoglycosidase H resistant molecules. In contrast, class I heavy chains synthesized in AD169 -infected cells were reported to be entirely endoglycosidase H sensitive (Beersma et al., 1993). As shown in FIG. 7, class I heavy chains synthesized in RV798-infected HFF cells, either at early or late times post-infection, were converted to the mature endoglycosidase H-resistant form at a rate similar to those synthesized in uninfected cells. Taken together, these data indicate that MHC class I synthesis, processing, and surface expression are not impaired in cells infected with these HCMV mutants. Furthermore, the results indicate that the 7-kb region containing US2-US11 genes contain one or more genes required for heavy chain down-regulation by HCMV.

Two Subregions Within the US2-US11 Gene Region Contain Genes Which are Involved in Class I Heavy Chain Down-Regulation The region of the HCMV genome deleted in RV35 was from US6-US11, and US2-US11 in RV798 (FIG. 1). In RV35-infected HFF cells, MHC class I heavy chains were down-regulated, but in RV798-infected cells they were not (FIG. 5A). This data indicates that one or more genes involved in heavy chain down-regulation maps within the 2-kb subregion from ORF US2 through US5 (subregion A; bases 193119–195607). To determine if this 2-kb subregion is required for class I heavy chain down-regulation, HCMV replacement mutants RV7181 and RV7177 were examined. HCMV ORFs IRS1-US9 and IRS1-US6 are deleted, respectively, in these mutants (FIG. 1); hence, subregion A is absent from both mutants. Experiments in infected HFF cells at late times post-infection indicated that both mutants retained the ability to efficiently down-regulate class I heavy gene expression (FIG. 8). Therefore, when present in the HCMV genome, gene(s) within subregion A are sufficient for reduction of MHC expression (e.g., RV35), although their presence is not required for the phenotype. Furthermore, the cumulative data (summarized in FIG. 9) indicate that there are no HCMV genes within the identified 7-kb US2-US11 region (i.e., the region deleted in RV798) which are absolutely required for efficient heavy chain down-regulation in infected HFF cells, suggesting that gene (s) from another portion of the US2-US11 gene region are also sufficient for the phenotype at late times post-infection.

Figure 8A:
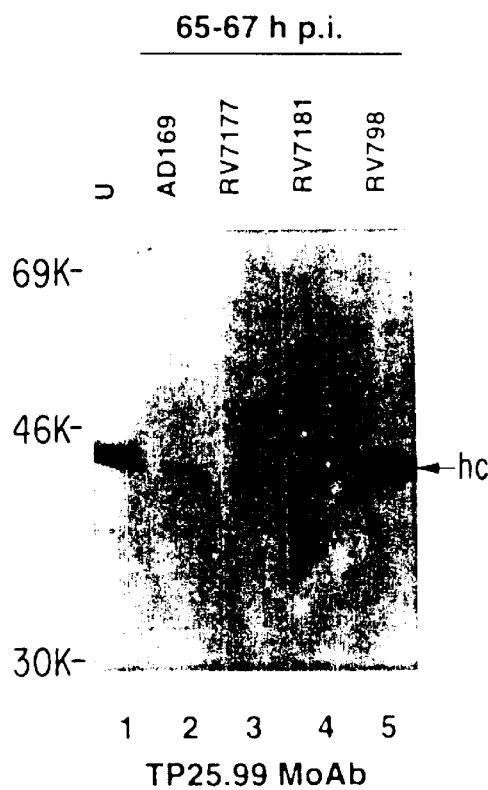
FIGS. 8A–8C show the immunoprecipitation of class I heavy chains from RV798-, RV7181-, RV7177-, or AD169 wild-type-infected cells. HFF cells were uninfected (U) or infected with the indicated virus (multiplicity of infection of 5 PFU/cell) and radiolabeled for 2 h at late times post-infection (65–67 h). Proteins were harvested immediately after radiolabeling.
Figure 8C:
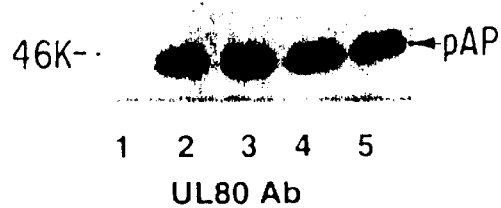
Figure 8B:
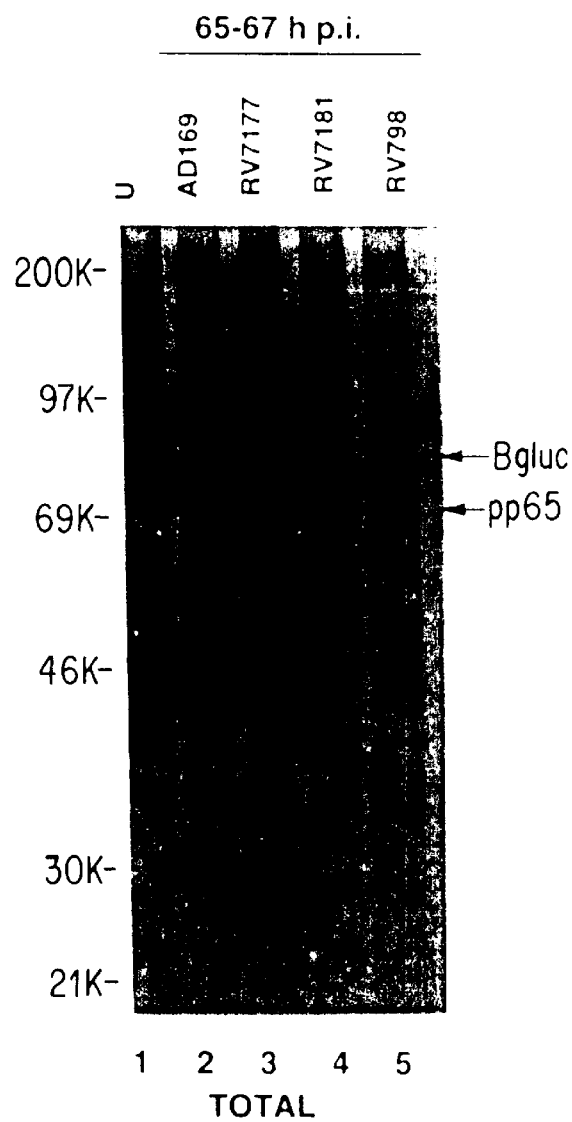

Evidence Indicating That the US11 Gene Product is Involved in MHC Class I Heavy Chain Down-Regulation In HFF cells infected with mutant RV7181, deleted from IRS1-US9 (FIG. 1), MHC class I heavy chain expression was down-regulated, in contrast to RV798-infected HFF cells (FIG. 8A). This data suggests that a second subregion (subregion B), comprised of the US10 and US11 genes (bases 199083–200360), is involved in reduction of heavy chain expression. However, the expression of US10 from the context of the HCMV genome is not sufficient for heavy chain down-regulation. HCMV mutant RV670 expressed US10 at steady-state levels similar to wild-type and was deleted of all of the other ORFs in the 7-kb US2-US11 gene region, but it did not cause down-regulation of MHC class I heavy chains in infected HFF cells (FIG. 5A). Thus, US11 is the gene in subregion B which is implicated by this genetic data.

US11 encodes a 32-kDa glycoprotein (gpUS11) containing N-linked, but not O-linked, carbohydrates which are completely sensitive to endoglycosidase H, indicating that the sugars are in the high mannose form. gpUS11 was detected throughout infection, beginning at very early times (i.e. 3 h) and continuing through late times post-infection. However, levels of gpUS11 in the infected cell are most abundant at approximately 8 h post-infection. To determine its location in the infected cell, rabbit polyclonal antisera (Jones and Muzithras, 1991) was used in immunofluorescence assays of wild-type strain AD169-infected cells. Uninfected and RV699-infected HFF cells were used as negative controls. RV699 is an HCMV mutant which is isogeneic with AD169, except for a deletion of the US11 ORF (Jones et al., 1991). In cells fixed and permeabilized at 8 h post-infection, cytoplasmic fluorescence which obscured definition of the nucleus was observed in AD169-infected HFF cells, but not in either negative control cells (FIGS. 10A and 10C, respectively). In general, the specific fluorescence was more intense in the perinuclear area. There was no specific fluorescence detected in non-permeabilized cells (FIGS. 10B and 10D). The fluorescence and endoglycosidase-H sensitivity data indicate that gpUS11 is not a cell surface glycoprotein. From the translated DNA sequence, gpUS11 is predicted to have hydrophobic domains near its N- and C-termini (Weston and Barrell, 1986) which are putative signal sequence and transmembrane domains, respectively. Thus, gpUS11 is associated with intracytoplasmic membranes, possibly the endoplasmic reticulum or cis golgi.

Evidence Indicating That the US2 Gene Product is Involved in MHC Class I Heavy Chain Down-Regulation Class I heavy chains were down-regulated in RV35-infected cells, but not in RV798-infected cells (FIGS. 11 and 12). To define the HCMV gene within subregion A (i.e., US2-US5) which is sufficient for MHC class I heavy chain down-regulation, several additional HCMV deletion mutants were constructed and analyzed. These new mutants included RV8146 and RV8173, which were deleted of the gene regions US4-US11 and US3-US11, respectively (FIG. 2). The new mutants were constructed using the previously described homologous recombination technique. Class I heavy chain expression in cells infected by these viruses was assayed in metabolic radiolabeling-immunoprecipitation experiments. Unlike RV798 infected cells, MHC class I heavy chains were down-regulated in cells infected with RV8146 and RV8173 (FIG. 11). The cumulative data derived from these experiments indicated that genes encompassing US3-US5 are not required for class I heavy chain down-regulation. Since the genotypic difference between mutants RV798 and RV8173 is the presence of US2 in the latter, US2 was therefore implicated in these genetic experiments.

Figure 13A:
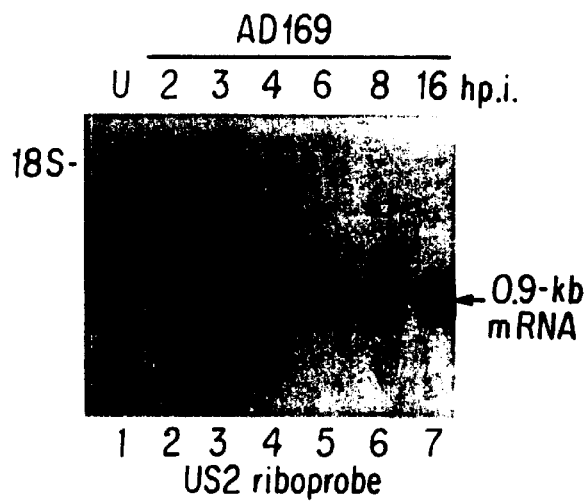
FIGS. 13A–13D show RNA and protein expression from US2. In all the experiments depicted in FIGS. 13A–D, the multiplicity of infection was 5. For FIGS. 13A and 13B, total cytoplasmic RNA was harvested from uninfected (U) or infected HFF at the indicated hour post-infection (h p.i.), electrophoresed in 1.2% agarose, transferred to nylon membranes, and hybridized with a US2-specific single-stranded riboprobe (i.e. Northern blot analysis). Cells were infected with either HCMV wild-type (AD169) or the US11–US2 deletion mutant RV798, as indicated. The 72 h p.i. RNA sample from RV798-infected cells (FIG. 13B, lane 7) was included as a negative control and thereby establishes validity to the small amount of the 0.9-kb US2 mRNA detected in the 72 h p.i. sample from AD169 (FIG. 13B, lane 6). For FIG. 13C, total cellular proteins from uninfected (U) or HCMV wild-type-infected (AD169) HFF cells at the indicated h p.i. were electrophoresed in 15% SDS-PAGE, transferred to nitrocellulose membranes, and probed with anti-US2 polyclonal antisera (i.e., Western blot analysis). The position of the ~24-kDa US2-encoded protein (pUS2) is indicated. For FIG. 13D, Western Blot analysis from HCMV wild-type- and mutant-infected cells was performed as described for FIG. 13C, except that all infected cell proteins were harvested at 11 h p.i.
Figure 13B:
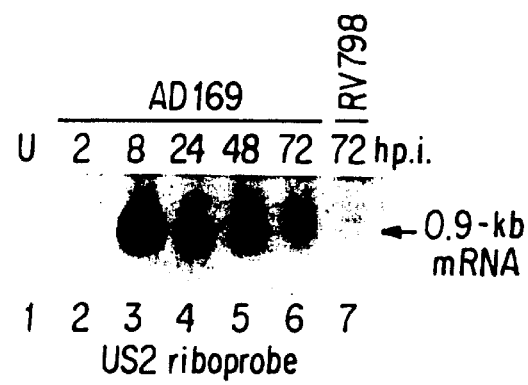
Figure 13C:
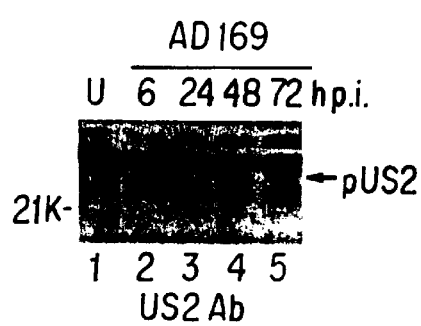
Figure 13D:
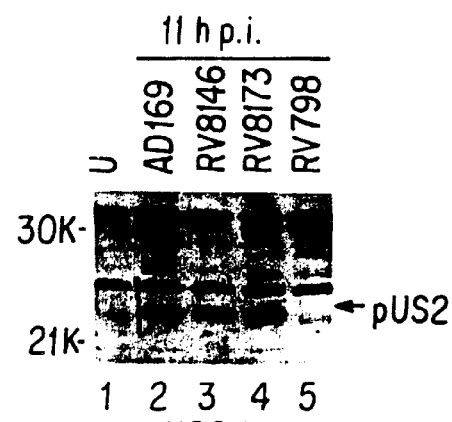

RNA blot analyses indicated that the US2 gene is transcribed throughout most of the HCMV replicative cycle, from very early times (e.g., 3 h) to late times (e.g., 72 h) post-infection (FIGS. 13A and 13B). To analyze US2 protein (pUS2) expression directly, a GST-US2 fusion protein was made in bacteria and used as an immunogen in rabbits for the generation of polyclonal antisera reactive with pUS2. This antisera reacted with an approximately 24-Kda protein which was expressed throughout the replicative cycle in cells infected with HCMV wild-type strain AD169 (FIG. 13C). The apparent mass of the pUS2 in these experiments correlated well with the 23.1-Kda computer-calculated molecular mass of the US2 protein derived from the translated US2 DNA sequence (Chee et al., 1990). The results from the genetic experiments described above predicted that pUS2 is expressed by cells infected with deletion mutants RV8146 and RV 8173, but not by RV798. Western Blot analysis of infected cell proteins confirmed this prediction (FIG. 13D).

Figure 14A:
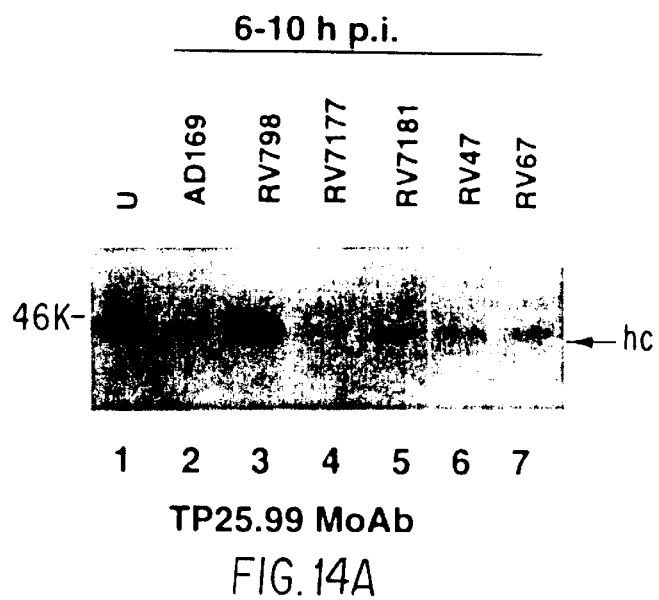
FIGS. 14A–14D show analysis of heavy chain expression in cells infected with HCMV mutants at early times post-infection. HFF cells were uninfected (U) or infected with the indicated virus (multiplicity of infection of 5 PFU/cell) and radiolabeled for 4 h from 6–10 h post-infection. Proteins were harvested immediately after radiolabeling.
Figure 14B:
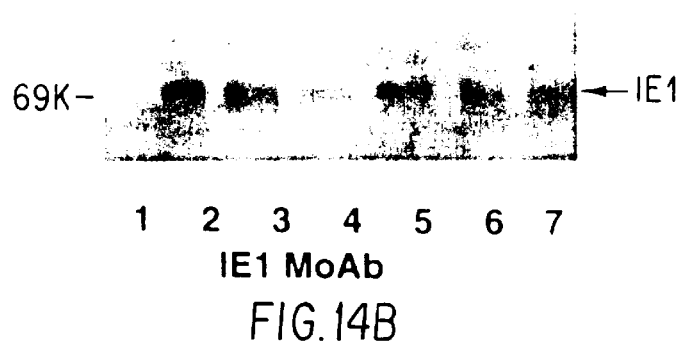
Figure 14C:
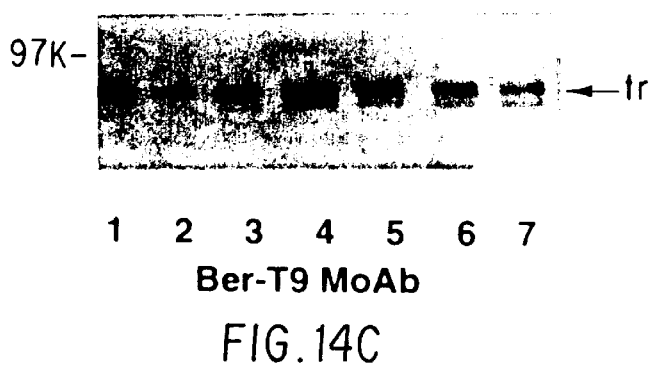
Figure 14D:
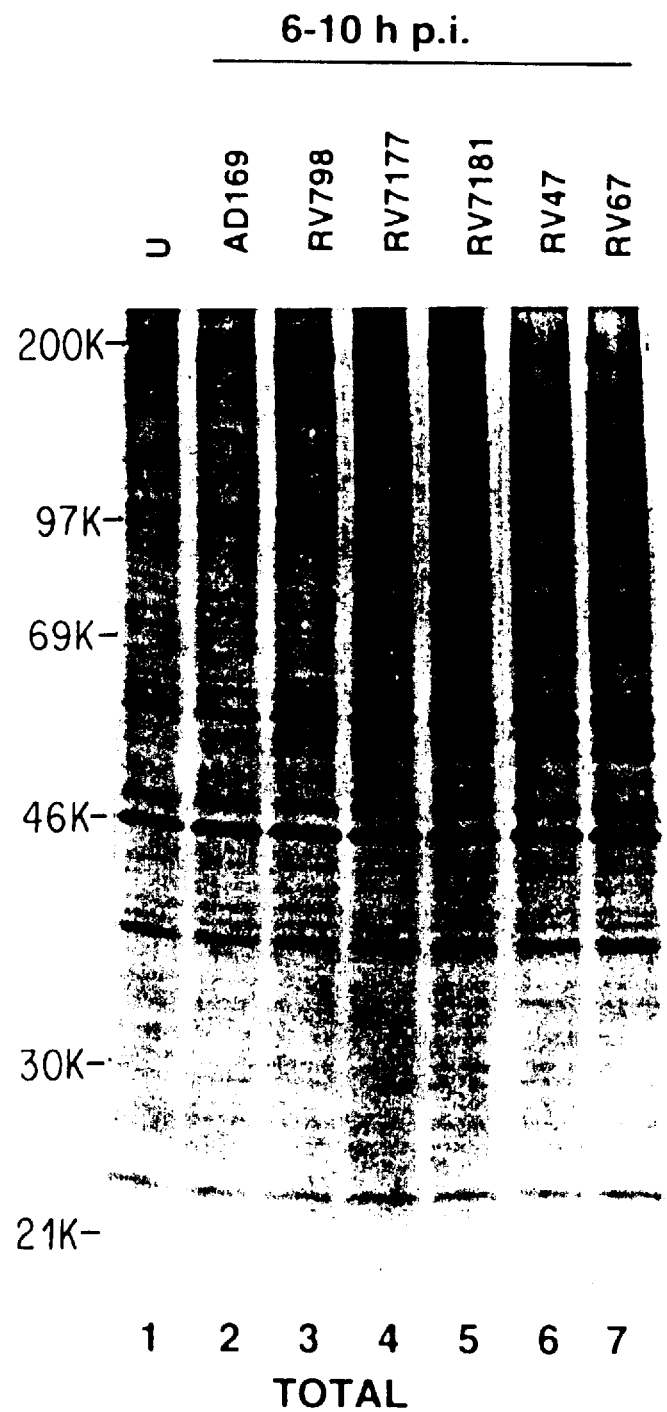

Down-Regulation of MHC Class I Expression at Early Times Post-infection by HCMV Mutants Down-regulation of MHC class I expression in wild-type strain AD169-infected cells are shown to begin at very early times post-infection (FIG. 4C). To determine if any of the mutants are deficient for this early down-regulation, immunoprecipitation experiments were performed using extracts from infected HFF cells radiolabeled from 6–10 h post-infection. The level of class I heavy chains were reduced during this early period post-infection in HFF cells with each of the mutants, except for RV798, the mutant deleted of the entire 7-kb US2-US11 region (FIG. 14A). Control experiments demonstrated that the different mutant-infected cells were equally infected and radiolabeled (FIG. 14B and D). Expression of another cellular glycoprotein, the transferrin receptor, was not differentially affected by the various mutants (FIG. 14C). Thus, genes required for heavy chain down-regulation at early times post-infection are the same as those necessary for reduction at late times post-infection. Moreover, expression of gene(s) from either subregion identified to be involved in down-regulation of heavy chain expression at late times post-infection are sufficient for reduction at very early times post-infection.

EXAMPLE 3

Recombinant HCMV (RV798) Vaccine Preparation

HCMV vaccines were prepared using a method described previously (Elek and Stern, 1974). HCMV mutant RV798 was grown on MRC-5 human diploid lung fibroblasts (CCL171 [American Type Culture Collection]) or human foreskin fibroblasts (MRHF [BioWhittaker]). Cells were infected at a multiplicity of infection equal to one in Dulbecco's modified Eagle medium (DMEM) containing 5% calf serum and 5% fetal calf serum. After 24 h, the medium was removed and the cells washed three times with either Hank's balanced salt solution or Dulbecco's phosphate-buffered saline. Fresh DMEM medium without serum was added; the infected cells were incubated 4 days after the appearance of late viral cytopathic effect (usually 7 days post-infection). After a preclearing centrifugation step (6,000×g for 20 minutes at 18° C.), cell-free virus was pelleted by centrifugation at 15,500×g for one hour at 18° C. The pelleted virus was resuspended in Dulbecco's phosphate-buffered saline containing 25% sorbitol and stored in aliquots at −70° C. The titer of RV798 vaccine stock is determined using standard procedures on human foreskin fibroblasts (Wentwork and French, 1970). The vaccine is administered by subcutaneous inoculation of approximately $10^3$–$10^7$ plaque forming units into the deltoid region of the upper arm, as described previously (Elek and Stern, 1974; Gehrz et al., 1980; Starr et al., 1981).

EXAMPLE 4 gpUS11 is Sufficient for Down-Regulation of MHC Class I Heavy Chains

The genetic data from the deletion virus-infected cells in Example 2 indicated that US11 is the gene within subregion B (i.e., US10-US11) of HCMV involved in MHC class I heavy chain down-regulation. To determine if the US11 gene product, in the absence of any other viral gene products, is capable of causing heavy chain down-regulation, the US11 coding region (bases 200360–199716 [Chee et al., 1990]) and some non-coding flanking sequences, encompassing bases 200391–199683, were cloned into a eukaryotic expression plasmid under the transcriptional control of the constitutive HCMV major immediate-early enhancer-promoter. Human U373-MG astrocytoma cells (HTB 17 [American Type Culture Collection]) were transfected with this plasmid (Sambrook et al, 1989) and stably-transfected cells were selected in the presence of 0.375 µg/ml of puromycin, since the plasmid also encodes for the prokaryotic puromycin resistance gene. Clones were picked and expanded into cell lines. Those expressing gpUS11 were identified by Western Blot analysis; different cell lines expressed varying amounts of US11. MHC class I heavy chain expression in these cell lines was analyzed in a similar fashion. As shown in FIG. 15, expression of US11 was inversely correlated with the expression of class I heavy chains. These data prove that expression of HCMV US11 is sufficient for the down-regulation of MHC class I heavy chain expression in the absence of any other viral gene products.

EXAMPLE 5 pUS2 is Sufficient for Down-Regulation of MHC Class I Heavy Chains

The genetic data from the deletion virus-infected cells in Example 2 indicated that US2 is the gene within subregion A (i.e., US2-US5) of HCMV involved in MHC class I heavy chain down-regulation. To confirm this indication, stably-transfected cells which constitutively express pUS2 were created. In this case, the HCMV US2 coding region (bases 193715 to 193119), and some non-coding flanking sequences, encompassing bases 193779 to 193003, were cloned into an expression vector plasmid designated plEsp-puro to yield plEspUS2-puro. In this plasmid, US2 was under the transcriptional control of the constitutive HCMV major immediate-early enhancer-promoter. This plasmid also contained a puromycin resistance gene expression cassette. After transfection of the plasmid into U373-MG astrocytoma cells, stably-transfected cell lines were selected and cloned in the presence of the drug puromycin (0.375 µg/ml). As a negative control, a similar plasmid (plEspBgluc-puro), which contains the prokaryotic β-glucuronidase gene instead of US2, was transfected and cell lines were selected and cloned. Steady-state protein expression in these cell lines was analyzed by Western blot analysis.

Figure 16A:
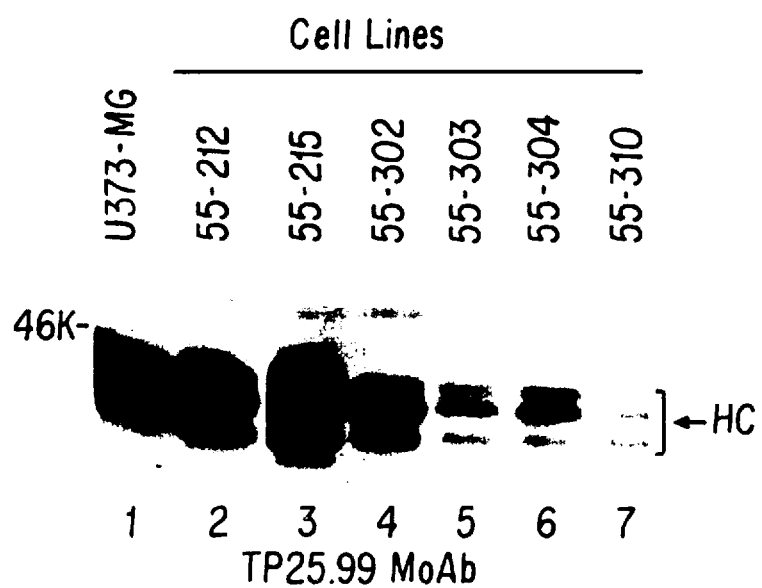
FIGS. 16A–16B show Western blot analysis of stably-transfected cell proteins. Total protein extracts from either U373-MG parental or stably-transfected (55 series) cells were electrophoresed and blotted as described for FIG. 13C. The blot was cut horizontally such that the portion of the blot containing MHC class I heavy chains (HC) were analyzed using the heavy chain monoclonal antibody TP25.99 (FIG. 16A), and the portion of the blot containing the US2-encoded protein (pUS2) were analyzed using the US2 polyclonal antibody (FIG. 16B). 55-212 and 55-215 are negative cell lines. Cell line 55-302, although transfected with the US2 expression plasmid does not express detectable amounts of pUS2. Cell lines 55-303, 55-304, and 55-310 express readily detectable amounts of pUS2. The cumulative data indicate the inverse relationship between levels of pUS2 and MHC class I heavy chains.
Figure 16B:
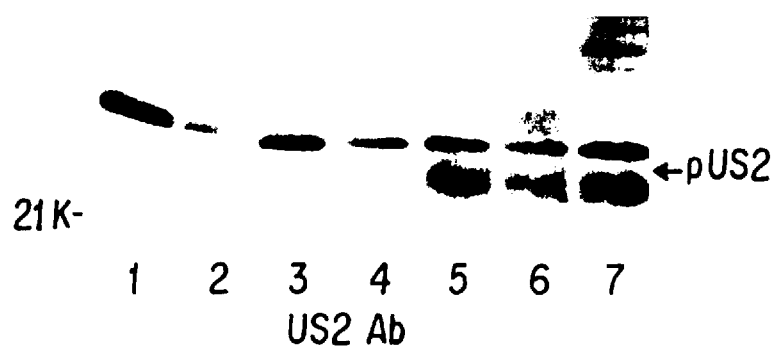

Similar to the US11-expressing cell lines of Example 4, the expression of US2 was found to be inversely correlated with expression of the cellular MHC class I heavy chains. Specifically, parental U373-MG cells and cell lines 55-212 and 55-215 derived from the transfection of the negative control plasmid did not express US2 and had high levels of class I heavy chains (FIG. 16, lanes 1–3). Cell lines 55-303, 55-304, and 55-310 were transfected with plEspUS2-puro and expressed US2, but had relatively low levels of class I heavy chains (FIG. 16, lanes 5–7). Another cell line derived from the transfection of plEspUS2-puro, 55-302, did not express US2 (presumably due to the disruption of the US2 gene during the generation of this cell line), but expressed high levels of class I heavy chain (FIG. 16, lane 4). The cumulative data demonstrated that US2 expression causes down-regulation of MHC class I heavy chain expression.

Figure 17A:
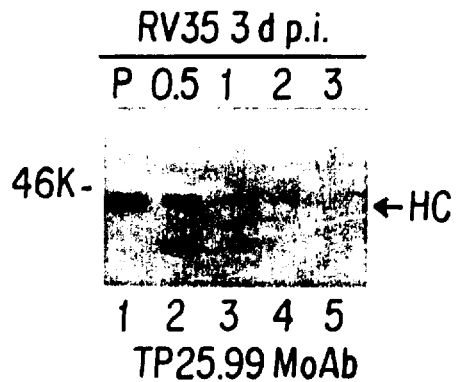
FIGS. 17A–17C show the instability of class I heavy chains in the presence of pUS2.
Figure 17B:
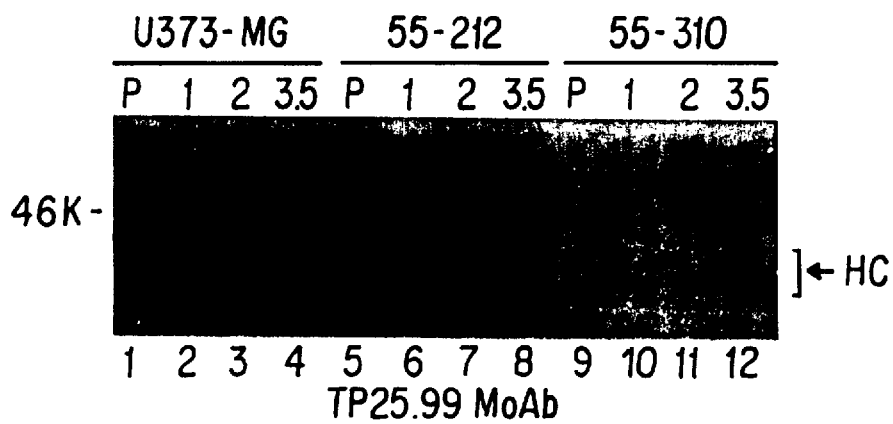
Figure 17C:
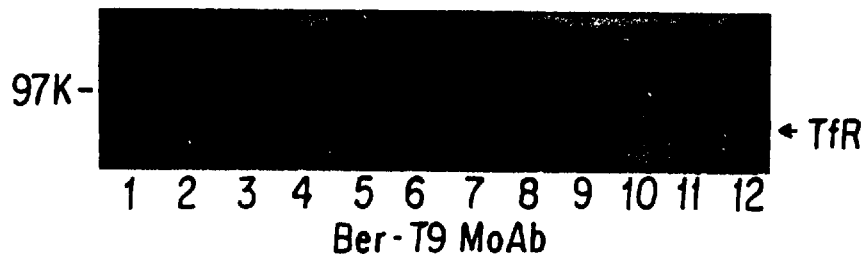

Data from HCMV-infected cells indicated that MHC class I heavy chains are down-regulated by a post-transcriptional mechanism resulting in the increased turnover (i.e., shorter half-life) of these proteins (Beersma et al., 1994; Yamashita et al., 1994). In cells infected with mutant RV35 (deleted of US6-US11 and containing the US2-US5 locus), the half-life of class I heavy chains is about 0.5 h, while the half-life in uninfected and RV798-infected cells is >3 h (FIG. 17A). Since US2 is the gene involved in class I heavy chain down-regulation within the US2-US5 locus, class I heavy chains in the stably-transfected US2-expressing cell lines were expected to have a high turnover rate compared to parental U373-MG cells and negative control cell lines. To test this prediction, representative cell lines of each type were "pulse" metabolically radiolabeled for 0.5 h with $^{35}$S-methionine/cysteine-containing media, and then either harvested immediately or "chased" in unlabeled media for various times prior to harvesting. Immunoprecipitation experiments using the pulse-chase extracts indicated that class I heavy chains were stable (half-life>3.5 h) in parental U373-MG cells and the negative control cell line 55-212 (FIG. 17B, lanes 1–4 and 5–8, respectively). In contrast, class I heavy chains had a very short half-life in the US2-expressing cell line 55-310 (FIG. 17B, lanes 9–12), as evidenced by the detection of heavy chains only in the pulse sample.

REFERENCES

1. Alford, C. A., and W. J. Britt. 1990. Cytomegalovirus, p. 1981–2010. In D. M. Knipe and B. N. Fields (ed.), Virology, 2nd ed. Raven press, New York.

2. Anderson, M., S. Paabo, T. Nilsson, and P. A. Peterson. 1985. Impaired intracellular transport of class I MHC antigens as a possible means for adenoviruses to evade immune surveillance. Cell 43:215–222.

3. Beck, S., and B. G. Barrell. 1988. Human cytomegalovirus encodes a glycoprotein homologous to MHC class I antigens. Nature 331:269–272.

4. Beersma, M. F. C., M. J. E. Bijlmakers, and H. L. Ploegh. 1993. Human cytomegalovirus down-regulates HLA class I expression by reducing the stability of class I H chains. J. Immunol. 151:4455–4464.

5. Browne, H., M. Churcher, and T. Minson. 1992. Construction and characterization of a human cytomegalovirus mutant with the UL18 (class I homolog) gene deleted. J. Virol. 66:6784–6787.

6. Browne, H., G. Smith, S. Beck, and T. Minson. 1990. A complex between the MHC class I homolog encoded by human cytomegalovirus and β2 microglobulin. Nature 347:770–772.

7. Burgert, H. G., and S. Kvist. 1985. An adenovirus type 2 glycoprotein blocks cell surface expression of human histocompatibility class I antigens. Cell 41:987–997.

8. Campbell, A. E., J. S. Slater. 1994. Down-regulation of major histocompatibility complex class I synthesis by murine cytomegalovirus early gene expression. J. Virol. 68:1805–1811.

9. Campbell, A. E., J. S. Slater, V. J. Cavanaugh, and R. M. Stenberg. 1992. An early event in murine cytomegalovirus replication inhibits presentation of cellular antigens to cytotoxic T lymphocytes. J. Virol. 66:3011–3017.

10. Chee, M. S., A. T. Bankier, S. Beck, R. Bohni, C. M. Brown, R. Cerny, T. Horsnell, C. A. Hutchinson, T. Kouzarides, J. A. Martignetti, E. Preddie, S. C. Satchwell, P. Tomlinson, K. Weston, and B. G. Barrell. 1990. Analysis of the protein-coding content of the sequence of human cytomegalovirus strain AD169. Curr. Top. Microbiol. Immunol. 154:125–169.

11. Colberg-Poley, A. M., L. D. Santomenna, P. P. Harlow, P. A. Benfield, and D. J. Tenney. 1992. Human cytomegalovirus US3 and UL36-38 immediate-early proteins regulate gene expression. J. Virol. 66:95–105.

12. del Val, M., K. Munch, M. Reddehasse, and U. Koszinowski. 1989. Presentation of CMV immediate-early antigen to cytotoxic T lymphocytes is selectively prevented by viral genes expressed in the early phase. Cell 58:305–315.

13. D'Urso, C. M., Z. Wang, Y. Cao, R. Tatake, R. A. Zeff, and S, Ferrone. 1991. Lack of HLA class I antigen expression by cultured melanoma cells FO-1 due to a defect in β2m gene expression. J. Clin. Invest. 87:284–292.

14. Elek, S. D., and H. Stern. 1974. Development of a vaccine against mental retardation caused by cytomegalovirus infection in utero. Lancet 1:1–5.

15. Gehrz, R. C., W. R. Christianson, K. M. Linner, K. E. Groth, and H. H. Balfour, Jr. 1980. Cytomegalovirus vaccine: specific humoral and cellular responses in human volunteers. Arch. intern. Med. 140:936–939.

16. Gilbert, M. J., S. R. Riddell, C-R. Li, and P. D. Greenberg. 1993. Selective interference with class I major histocompatibility complex presentation of the major immediate-early protein following infection with human cytomegalovirus. J. Virol. 67:3461–3469.

17. Gooding, L. R. 1992. Virus proteins that counteract host immune defenses. Cell 71:5–7.

18. Gretch, D. R., and M. F. Stinski. 1990. Transcription of the human cytomegalovirus glycoprotein gene family in the short unique component of the viral genome. Virology 174:522–532.

19. Jones, T. R., and Muzithras, V. P. 1991. Fine mapping of transcripts expressed from the US6 gene family of human cytomegalovirus strain AD169. J. Virol. 65:2024–2036.

20. Jones, T. R., and V. P. Muzithras. 1992. A cluster of dispensable genes within the human cytomegalovirus genome short component: IRS1, US1 through US5, and the US6 family. J. Virol. 66:2541–2546.

21. Jones, T. R., V. P. Muzithras, and Y. Gluzman. 1991. Replacement mutagenesis of the human cytomegalovirus genome: US10 and US11 gene products are nonessential. J. Virol. 65:5860–5872.

22. Jones, T. R., L. Sun, G. A. Bebernitz, V. P. Muzithras, H-J. Kim, S. H. Johnston, and E. Z. Baum. 1994. Proteolytic activity of human cytomegalovirus UL80 protease cleavage site mutants. J. Virol. 68:3742–3752.

23. Jonjic, S., M. de Val, G. M. Keil, M. J. Reddehasse, and U. Koszinowski. 1988. A nonstructural viral protein expressed by a recombinant vaccinia virus protects against lethal cytomegalovirus infection. J. Virol. 62:1653–1658.

24. Mavromara-Nazos, P., M. Ackerman, and B. Roizman. 1986. Construction and properties of a viable herpes simplex virus 1 lacking coding sequences of the alpha 47 gene. J. Virol 60:807–812.

25. McKnight, S. L. 1980. The nucleotide sequence and transcript map of the herpes simplex virus thymidine kinase gene. Nucl. Acids Res. 8:5949–5964.

26. Oram, J. D., R. G. Downing, A. Akrigg, A. A. Dollery, C. J. Duggleby, G. W. G. Wilkinson, and P. J. Greenaway. 1982. Use of recombinant plasmids to investigate the structure of the human cytomegalovirus genome. J. Gen. Virol. 59:111–129.

27. Sambrook, J., E. F. Fritsch, and T. Maniatis. 1989. Molecular cloning: a laboratory manual, 2nd ed. Cold Spring Harbor Laboratory Press, Cold Spring Harbor, N.Y.

28. Schwartz, R. H. 1985. T lymphocyte recognition of antigen in association with gene products of the major histocompatibility complex. Ann. Rev. Immunol. 3:237–261.

29. Starr, S. E., J. P. Glazer, H. M. Friedman, J. D. Farquhar, and S. A. Plotkin. 1981. Specific cellular and humoral immunity after immunization with live Towne strain cytomegalovirus vaccine. J. Infect. Dis. 143:585–589.

30. Tenney, D. J., and A. M. Colberg-Poley. 1991. Human cytomegalovirus UL36-38 and US3 immediate-early genes: temporally regulated expression of nuclear, cytoplasmic, and polysome-associated transcripts during infection. J. Virol. 65:6724–6734.

31. Tenney, D. J., L. D. Santomenna, K. B. Goudie, and A. M. Colberg-Poley. 1993. The human cytomegalovirus US3 immediate-early protein lacking the putative transmembrane domain regulates gene expression. Nucl. Acids Res. 21:2931–2937.

32. Wentworth, B. B., and French, L. 1979. Plaque assay of cytomegalovirus strains of human origin. Proc. Soc. Exp. Biol., Med. 135:253–258.

33. Weston, K. 1988. An enhancer element in the short unique region of human cytomegalovirus regulates the production of a group of abundant immediate early transcripts. Virology 162:406–416.

34. Weston, K., and B. G. Barrell. 1986. Sequence of the short unique region, short repeats, and parts of the long repeats of human cytomegalovirus. J. Mol. Biol. 192:177–208.

35. Yamashita, Y., K. Shimokata, S. Mizuno, H. Yamaguchi, and Y. Nishiyama. 1993. Down-regulation of the surface expression of class I MHC antigens by human cytomegalovirus. Virology 193:727–736.

36. Yamashita, Y., Shimokata, K., Saga, S., Mizuno, S. Tsurumi, T., and Nishiyama, Y. 1994. Rapid degradation of the heavy chain of class I major histocompatibility complex antigens in the endoplasmic reticulum of human cytomegalovirus-infected cells. J. Virol. 68:7933–7943.

37. York, I. A., C. Roop, D. W. Andrews, S. R. Riddell, F. L. Graham, and D. C. Johnson. 1994. A cytosolic herpes simplex virus protein inhibits antigen presentation to CD8+ T lymphocytes. Cell 77:525–535.

37. Zinkernagel, R. M., and P. C. Doherty. 1980. MHC restricted cytotoxic T cells: studies on the biological role of polymorphic major transplantation antigens determining T cell restriction specificity. Adv. Immunol. 27:51–177.

What is claimed is:

1. A method of producing a recombinant human cytomegalovirus comprising the step of deleting a gene sequence which consists of the gene sequence encoding open reading frame US2 from the genome of a human cytomegalovirus.

2. A recombinant human cytomegalovirus comprising a genome having a deletion of the gene sequence encoding open reading frame US2, wherein no other gene sequence has been deleted.

3. A pharmaceutical composition comprising the recombinant human cytomegalovirus of claim 2 and a pharmaceutically acceptable vehicle.

4. A vaccine composition for use in the prevention of cytomegalovirus infections which comprises an effective amount of the recombinant human cytomegalovirus of claim 2 in a pharmaceutically acceptable vehicle.

5. The vaccine composition of claim 4, further comprising an adjuvant.

6. A method of immunizing an individual against human cytomegalovirus comprising administering to the individual an immunogenic amount of the vaccine composition of claim 4.

\* \* \* \* \*